United States Patent
Wang et al.

(10) Patent No.: US 11,361,440 B2
(45) Date of Patent: Jun. 14, 2022

(54) METHOD AND SYSTEM FOR DIAGNOSIS OF COVID-19 DISEASE PROGRESSION USING ARTIFICIAL INTELLIGENCE

(71) Applicant: SHENZHEN KEYA MEDICAL TECHNOLOGY CORPORATION, Shenzhen (CN)

(72) Inventors: Xin Wang, Seattle, WA (US); Youbing Yin, Kenmore, WA (US); Bin Kong, Charlotte, NC (US); Yi Lu, Seattle, WA (US); Junjie Bai, Seattle, WA (US); Zhenghan Fang, Shoreline, WA (US); Qi Song, Seattle, WA (US)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 0 days.

(21) Appl. No.: 17/317,989

(22) Filed: May 12, 2021

(65) Prior Publication Data

US 2022/0039768 A1    Feb. 10, 2022

Related U.S. Application Data

(63) Continuation of application No. 17/067,181, filed on Oct. 9, 2020, now Pat. No. 11,076,824.

(Continued)

(51) Int. Cl.
*G06T 7/00*    (2017.01)
*A61B 6/00*    (2006.01)
(Continued)

(52) U.S. Cl.
CPC .......... *G06T 7/0012* (2013.01); *A61B 5/7267* (2013.01); *A61B 5/7275* (2013.01);
(Continued)

(58) Field of Classification Search
CPC ....... A61B 6/50; A61B 5/7267; A61B 5/7275; A61B 6/032; A61B 6/025; G06N 3/04;
(Continued)

(56) References Cited

U.S. PATENT DOCUMENTS 10,691,980 B1    6/2020 Guendel et al.
2018/0211153 A1  7/2018 Hunt et al.
(Continued)

FOREIGN PATENT DOCUMENTS

CN    111681219 A    9/2020
CN    111986189 A    11/2020

OTHER PUBLICATIONS

Xiao et al. "Development and Validation of a Deep Learning-Based Model Using Computed Tomography Imaging for Predicting Disease Severity of Coronavirus Disease 2019." Front Bioeng Biotechnol. 2020;8:898. Published Jul. 3, 20201.*

(Continued)

*Primary Examiner* — Amanda Lauritzen Moher
(74) *Attorney, Agent, or Firm* — Bayes PLLC

(57) ABSTRACT

Embodiments of the disclosure provide methods and systems for disease condition prediction from images of a patient. The system may include a communication interface configured to receive a sequence of images acquired of the patient by an image acquisition device. The sequence of images are acquired at a sequence of prior time points during progression of a disease. The system may include a processor, configured to determine regions of interest based on the sequence of images. The processor applies a progressive condition prediction network to the regions of interest to predict a level of disease progression at a future time point during the progression of the disease. The progressive condition prediction network predicts the level of disease progression based on the regions of interest and disease (Continued)

conditions at the sequence of prior time points. The processor further provides a diagnostic output based on the predicted level of disease progression.

20 Claims, 12 Drawing Sheets

Related U.S. Application Data

(60) Provisional application No. 63/063,114, filed on Aug. 7, 2020.

(51) Int. Cl.
```
A61B 5/00      (2006.01)
A61B 6/03      (2006.01)
G16H 50/20     (2018.01)
G16H 10/60     (2018.01)
G06N 3/04      (2006.01)
G06N 3/08      (2006.01)
G16H 30/40     (2018.01)
A61B 6/02      (2006.01)
```
(52) U.S. Cl.
CPC ............... *A61B 6/032* (2013.01); *A61B 6/50* (2013.01); *G06N 3/04* (2013.01); *G06N 3/08* (2013.01); *G16H 10/60* (2018.01); *G16H 30/40* (2018.01); *G16H 50/20* (2018.01); *A61B 6/025* (2013.01); *G06T 2207/10076* (2013.01); *G06T 2207/20081* (2013.01); *G06T 2207/20084* (2013.01); *G06T 2207/30061* (2013.01)

(58) Field of Classification Search
CPC .................... G06N 3/08; G06T 7/0012; G06T 2207/10076; G06T 2207/20081; G06T 2207/20084; G06T 2207/30061; G16H 10/60; G16H 30/40; G16H 50/20
See application file for complete search history.

(56) References Cited

U.S. PATENT DOCUMENTS

| | | | |
|---|---|---|---|
| 2019/0180441 A1* | 6/2019 | Peng | G06T 7/0016 |
| 2019/0220733 A1* | 7/2019 | Fisher | G06N 3/0454 |
| 2020/0349706 A1 | 11/2020 | Gao et al. | |
| 2022/0082574 A1* | 3/2022 | Watanabe | G01N 29/022 |

OTHER PUBLICATIONS

Weist. "Recurrent Neural Networks—Combination of RNN and CNN." Convolutional Neural Networks for Image and Video Processing: Technische Universität München, last modified Feb. 7, 2017, accessed Jan. 6, 2022.<https://wiki.tum.de/display/lfdv/Recurrent+Neural+Networks+-+Combination+of+RNN+and+CNN>.*
Xu et al. "GASNet: Weakly-supervised Framework for COVID-19 Lesion Segmentation." arXiv:2010.09456v1, Oct. 19, 2020.*
Li et al., "Using Artificial Intelligence to Detect COVID-19 and Community-acquired Pneumonia Based on Pulmonary CT: Evaluation of the Diagnostic Accuracy", Radiology 2020; vol. 296, No. 2, Aug. 2020, 8 pages.
Wang et al. "Chestx-ray8: Hospital-scale Chest X-ray Database and Benchmarks on Weakly-Supervised Classification and Localization of Common Thorax Diseases." Proceedings of the IEEE Conference on Computer Vision and Pattern Recognition: pp. 2019-2106 (2017).
Anthimopoulos et al. "Lung Pattern Classification for Interstitial Lung Diseases Using A Deep Convolutional Neural Network." IEEE Transactions on Medical Imaging: pp. 1207-1216 (2016).
Hoon et al. "COVI D-19 Pneumonia Diagnosis Using a Simple 2D Deep Learning Framework With A Single Chest CT Image." JMIR Preprint. Available on-line Apr. 23, 2020. Officially released as "COVI D-19 Pneumonia Diagnosis Using a Simple 2D Deep Learning Framework With a Single Chest CT Image" in vol. 22, No. 6: Jun. 2020.
Wang et al. "A Fully Automatic Deep Learning System for COVID-19 Diagnostic and Prognostic Analysis" Eur Respir J 2020. Available online May 22, 2020.
Cohen et al. "Predicting COVI D-19 Pneumonia Severity on Chest X-ray With Deep Learning." Cureus 12(7). Jul. 28, 2020.
Shoeibi et al. "Automated Detection and Forecasting of COVID-19 using Deep Learning Techniques: A Review" arXiv:2007.10785. Available online Jul. 27, 2020 (earlier versions available).
Yang et al. "End-to-end COVID-19 Screening With 3D Deep Learning On Chest Computed Tomography." DOI: https://doi.org/10.21203/rs.3.rs-36433/v1. Available online Jun. 18, 2020.
Ozturk et al. "Automated Detection of COVID-19 Cases Using Deep Neural Networks With X-ray Images" Computers in Biology and Medicine 121 (2020). Available online Apr. 28, 2020.
Jain et al. "A Deep Learning Approach to Detect Covid-19 Coronavirus with X-Ray Images ." Biocybernetics and Engineering (2020) 1391-1405. Available online Sep. 7, 2020.
Li et al. "Artificial Intelligence Distinguishes COVID-19 from Community Acquired Pneumonia on Chest CT." Radiology. Mar. 1, 20209 : 200905 Available online Mar. 19, 2020.
Li et al. "Using Artificial Intelligence to Detect COVID-19 and Community-acquired Pneumonia Based on Pulmonary CT: Evaulation of the Diagnostic Accuracy." Radiology 296(2). Available online Mar. 19, 2020.

* cited by examiner

METHOD AND SYSTEM FOR DIAGNOSIS OF COVID-19 DISEASE PROGRESSION USING ARTIFICIAL INTELLIGENCE

CROSS-REFERENCE TO RELATED APPLICATIONS

This application is a continuation of U.S. application Ser. No. 17/067,181, entitled "Method and System for Diagnosis of COVID19 Using Artificial Intelligence" and filed Oct. 9, 2020, which claims the benefit of priority to U.S. Provisional Application No. 63/063,114, filed on Aug. 7, 2020, the entire content of both of which is incorporated herein by reference.

TECHNICAL FIELD

The present disclosure relates to methods and systems for diagnosis of coronavirus disease 2019 (COVID-19) or other similar conditions from biomedical images, and more particularly to detecting COVID-19 or other lung conditions from chest images using deep learning networks.

BACKGROUND

Coronavirus disease 2019 (COVID-19) has widely spread all over the world since the end of 2019. COVID-19 is a highly contagious disease. Severe cases may result in an acute respiratory distress or multiple organ failure. On Jan. 30, 2020, the outbreak was declared as a "public health emergency of international concern" (PHEIC) by the world health organization (WHO). Early diagnosis of the disease is important for treatment and patient isolation to prevent further virus spread. The disease is typically confirmed by reverse-transcription polymerase chain reaction (RT-PCR). RT-PCR thereby is considered as a reference standard.

However, it has been recently reported that the sensitivity of RT-PCR might not be sufficient for the early detection and treatment of presumptive patients. On the other hand, non-invasive imaging approaches, such as computed tomography (CT) and X-ray, have been proven effective in diagnosis of COVID-19 and evaluation of the disease progression. For example, a chest CT image can capture characteristic manifestations in a lung associated with COVID-19. The abnormal CT findings in COVID-19 have been recently reported to include ground-glass opacification, consolidation, bilateral involvement, peripheral and diffuse distribution. Therefore, the chest CT image analysis can serve as an effective method for early screening and diagnosis of COVID-19. However, because COVID-19 and other types of pneumonia, e.g., Community Acquired Pneumonia (CAP), show similar imaging characteristics in chest CT images, accurate diagnosis usually has to rely on clinical experience of radiologists to distinguish COVID-19 from CAP and other pneumonia in chest CT images.

Diagnostic image analysis systems have been proposed to relieve heavy workloads and improve clinical decisions of radiologists. For example, artificial intelligence (AI) using deep learning technology has demonstrated great success in the diagnostic image analysis systems due to its high capability of feature extraction. Further, deep learning-based methods were applied to detect and differentiate bacterial and viral pneumonia in pediatric chest radiographs. However, existing diagnostic image analysis systems for diagnosing lung diseases are limited to performing a single medical diagnostic task such as COVID-19 detection, pneumonia lesion segmentation, disease severity assessment, follow-up condition prediction, etc., while unable to differentiate among these easily confusing conditions.

Embodiments of the disclosure address the above problems by methods and systems for multi-task diagnostic image analysis that provides a comprehensive diagnosis and assessment of COVID-19 and other lung conditions using deep learning networks.

SUMMARY

Novel methods and systems for diagnosis of COVID-19 from biomedical images, and more particularly, for detecting COVID-19 and other lung conditions in chest images using deep learning networks, are disclosed.

In one aspect, embodiments of the disclosure provide a system for disease condition prediction from images of a patient. The exemplary system may include a communication interface configured to receive a sequence of images acquired of the patient by an image acquisition device. The sequence of images are acquired at a sequence of prior time points during progression of a disease. The system may further include at least one processor, configured to determine regions of interest based on the sequence of images acquired at the sequence of prior time points. The at least one processor also applies a progressive condition prediction network to the regions of interest to predict a level of disease progression at a future time point during the progression of the disease. To apply the progressive condition network to the regions of interest, the at least one processor is configured to: predict the level of disease progression at the future time point based on disease conditions at the sequence of prior time points and the regions of interest by applying the progressive condition prediction network including a convolutional recurrent neural network (ConvRNN) layer, a recurrent neural network (RNN) layer separate from the ConvRNN layer and a plurality of fully connected layers receiving inputs from both the ConvRNN layer and the RNN layer. The at least one processor further provides a diagnostic output based on the predicted level of disease progression at the future time point.

In another aspect, embodiments of the disclosure also provide a method for disease condition prediction from images of a patient. The exemplary method includes receiving, by a communication interface, a sequence of images acquired of the patient by an image acquisition device. The sequence of images are acquired at a sequence of prior time points during progression of a disease. The method further includes determining, by at least one processor, regions of interest based on the sequence of images acquired at the sequence of prior time points. The method may further include applying, by the at least one processor, a progressive condition prediction network to the regions of interest to predict a level of disease progression at a future time point dining the progression of the disease. To apply the progressive condition network to the regions of interest, the method further includes predicting the level of disease progression at the future time point based on disease conditions at the sequence of prior time points and the regions of interest by applying the progressive condition prediction network including a ConvRNN layer, a RNN layer separate from the ConvRNN layer, and a plurality of fully connected layers receiving inputs from both the ConvRNN layer and the RNN layer. The method also includes providing a diagnostic output based on the predicted level of disease progression at the future time point.

In yet another aspect, embodiments of the disclosure further provide a method for COVID-19 condition prediction from lung images of a patient. The exemplary method includes receiving, by a communication interface, a sequence of lung images acquired of a lung of the patient by an image acquisition device. The sequence of images are acquired at a sequence of prior time points during progression of a COVID-19 disease. The method further includes determining, by at least one processor, regions of interest based on the sequence of lung images acquired at the sequence of prior time points, where each region of interest comprise the lung. The method also includes applying, by the at least one processor, a progressive condition prediction network to the regions of interest to predict a progression level of the COVID-19 disease at a future time point. To apply the progressive condition network to the regions of interest, the method further includes predicting the progression level of the COVID-19 disease at the future time point based on disease conditions at the sequence of prior time points and the regions of interest by applying the progressive condition prediction network including a ConvRNN layer, a RNN layer separate from the ConvRNN layer, and a plurality of fully connected layers receiving inputs from both the ConvRNN layer and the RNN layer. The method additionally includes providing a diagnostic output based on the predicted progression level of the COVID-19 disease at the future time point.

It is to be understood that both the foregoing general description and the following detailed description are exemplary and explanatory only and are not restrictive of the invention, as claimed.

DETAILED DESCRIPTION

Reference will now be made in detail to the exemplary embodiments, examples of which are illustrated in the accompanying drawings.

The disclosed methods and systems provide a three-dimensional (3D) deep learning-based framework including learning networks for detecting COVID-19, segmenting a lesion of the disease, assessing a severity of the disease, and predicting a follow-up condition of the disease. In some embodiments, a COVID-19 detection network may be applied on a 3D lung region of interest (ROI) to distinguish COVID-19 from other pneumonia or non-pneumonia lung conditions (including normal or abnormal conditions). In some embodiments, the 3D lung ROI may be obtained based on a 3D chest CT image. For example, a segmentation method using a fully convolutional neural network (FCN) may be used to preprocess the 3D lung CT image and extract a lung region as the lung ROI. The lung ROI can be presented in a 3D format (e.g., a 3D volumetric image) or 2D format (e.g., a series of 2D slices).

Figure 1A:
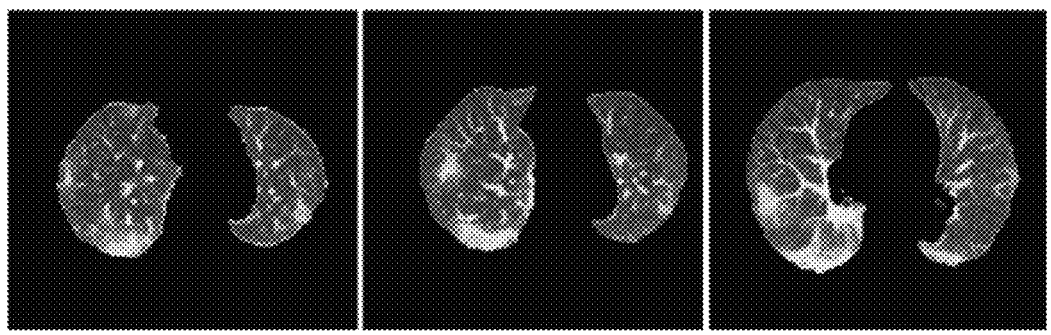
FIG. 1A illustrates three exemplary images of a lung region diagnosed as COVID-19.
Figure 1B:
FIG. 1B illustrates three exemplary image of lung ROI diagnosed as non-COVID-19 pneumonia.
Figure 1C:
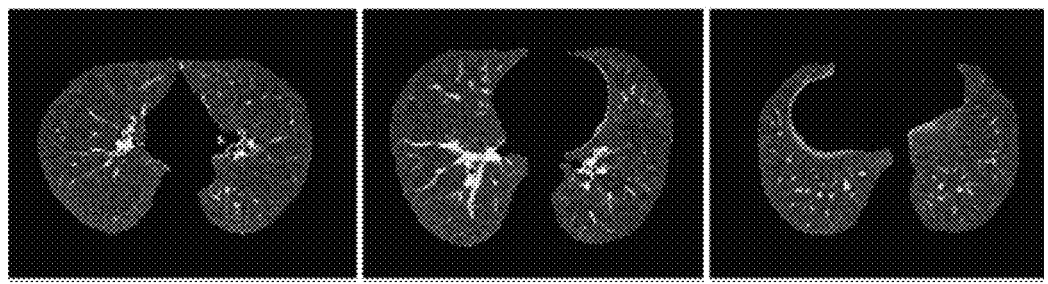
FIG. 1C illustrates three examples of lung region of a normal condition.

For example, FIG. 1A illustrates three exemplary images of a lung region diagnosed as COVID-19. The lung region is confirmed to contract COVID-19 by positive RT-PCR test. Each 2D image shown in FIG. 1A contains a slice of the 3D ROI of the lung region. The ROI images may be extracted from a 3D chest CT image. FIG. 1B illustrates three exemplary images of a lung region diagnosed as non-COVID-19 pneumonia. In some embodiments, the non-COVID-19 pneumonia may be community acquired pneumonia (CAP). FIG. 1C illustrates three exemplary images of a lung region of a normal condition. Image of FIGS. 1A and 1B show various lesion characteristics, Compared with FIGS. 1A and 1B, such as ground-glass opacification, consolidation, bilateral involvement, peripheral, or diffuse distribution. Images of FIG. 1C, on the other hand, do not include such lung lesions. Artificial intelligence systems and methods disclosed herein are designed to differentiate the different lung conditions based on the characteristics captured by the images.

In some embodiments, a diagnostic image analysis system may be configured to perform a diagnostic prediction (e.g., COVID-19 detection) based on a biomedical image. For example, the diagnostic image analysis system may receive the biomedical image (e.g. a 3D chest CT image) from an image acquisition device. The diagnostic image analysis system may further detect whether a certain abnormal lung condition, e.g., COVID-19, CAP, other non-pneumonia lung abnormalities, can be detected from the image. In addition to detecting a COVID-19, the diagnostic image analysis system may alternatively or additionally segment a lesion of the disease, assess a severity of the disease, and/or predict a follow-up condition of the disease.

Figure 2:
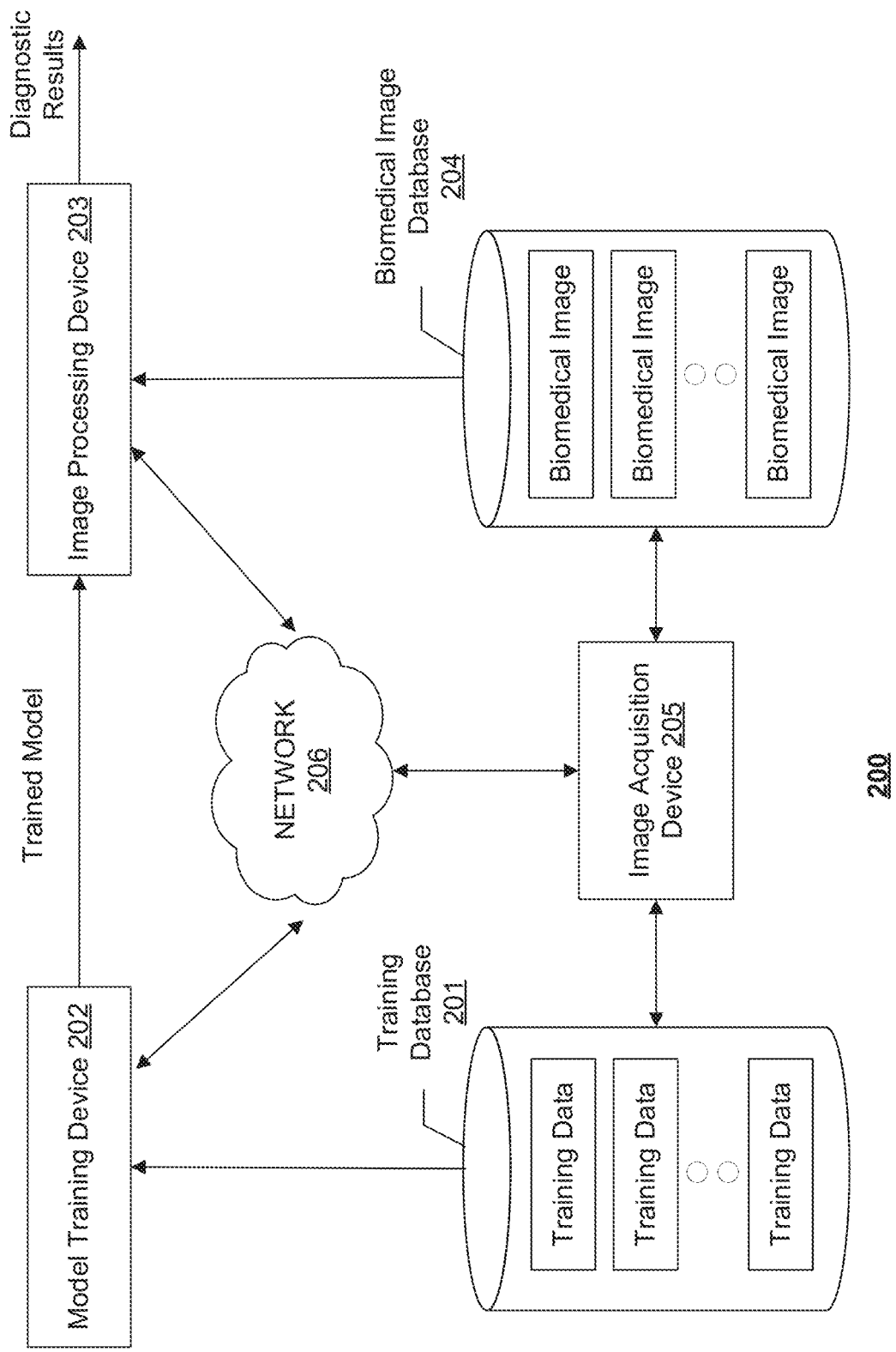
FIG. 2 illustrates a schematic diagram of an exemplary diagnostic image analysis system 200, according to certain embodiments of the disclosure.

FIG. 2 illustrates an exemplary diagnostic image analysis system 200, according to some embodiments of the present disclosure. Consistent with the present disclosure, diagnostic image analysis system 200 may be configured to analyze a biomedical image acquired by an image acquisition device 205 and perform a diagnostic prediction based on the image analysis. In some embodiments, image acquisition device 205 may be a CT scanner that acquires 2D or 3D CT images. For example, image acquisition device 205 may be a 3D cone CT scanner for volumetric CT scans. In some embodiments, image acquisition device 205 may be using one or more other imaging modalities, including, e.g., Magnetic Resonance Imaging (MRI), functional MRI (e.g., fMRT, DCE-MRI and diffusion MRI), Positron Emission Tomography (PET), Single-Photon Emission Computed Tomography (SPECT), X-ray, Optical Coherence Tomography (OCT), fluorescence imaging, ultrasound imaging, radiotherapy portal imaging, or the like.

In some embodiments, image acquisition device 205 may capture images containing at least one anatomical structure or organ, such as a lung or a thorax. In some embodiments, each volumetric CT exam may contain 51~1094 CT slices with a varying slice-thickness from 0.5 mm to 3 mm. The reconstruction matrix may have 512×512 pixels with in-plane pixel spatial resolution from $0.29 \times 0.29$ mm$^2$ to $0.98 \times 0.98$ mm$^2$.

As shown in FIG. 2, diagnostic image analysis system 200 may include components for performing two phases, a training phase and a prediction phase. The prediction phase may also be referred to as an inference phase. To perform the training phase, diagnostic image analysis system 200 may include a training database 201 and a model training device 202. To perform the prediction phase, diagnostic image analysis system 200 may include an image processing device 203 and a biomedical image database 204. In some embodiments, diagnostic image analysis system 200 may include more or less of the components shown in FIG. 2. For example, when a diagnosis model for providing a diagnostic prediction based on the biomedical images is pre-trained and provided, diagnostic image analysis system 200 may include only image processing device 203 and biomedical image database 204.

Diagnostic image analysis system 200 may optionally include a network 206 to facilitate the communication among the various components of diagnostic image analysis system 200, such as databases 201 and 204, devices 202, 203, and 205. For example, network 206 may be a local area network (LAN), a wireless network, a cloud computing environment (e.g., software as a service, platform as a service, infrastructure as a service), a client-server, a wide area network (WAN), etc. In some embodiments, network 206 may be replaced by wired data communication systems or devices.

In some embodiments, the various components of diagnostic image analysis system 200 may be remote from each other or in different locations, and be connected through network 206 as shown in FIG. 2. In some alternative embodiments, certain components of diagnostic image analysis system 200 may be located on the same site or inside one device. For example, training database 201 may be located on-site with or be part of model training device 202. As another example, model training device 202 and image processing device 203 may be inside the same computer or processing device.

Model training device 202 may use the training data received from training database 201 to train a diagnosis model for analyzing a biomedical image received from, e.g., biomedical image database 204, in order to provide a diagnostic prediction. As shown in FIG. 2, model training device 202 may communicate with training database 201 to receive one or more sets of training data. In certain embodiments, each set of training data may include ground truth of disease type labels (e.g., lung condition), lesion masks, disease severity labels, patient information, testing results, and ongoing treatment information.

Training images stored in training database 201 may be obtained from a biomedical image database containing previously acquired images of anatomical structures. In some embodiments, the biomedical image may be processed by model training device 202 to identify specific diseases (e.g., COVID-19), anatomical structures, support structures, and other items. The prediction results are compared with an initial diseases/finding probability analysis, and based on the difference, the model parameters are improved/optimized by model training device 202. For example, an initial diseases/findings probability analysis may be performed and verified by experts.

In some embodiments, the training phase may be performed "online" or "offline." An "online" training refers to performing the training phase contemporarily with the prediction phase, e.g., learning the model in real-time just prior to analyzing a biomedical image. An "online" training may have the benefit to obtain a most updated learning model based on the training data that is then available. However, an "online" training may be computational costive to perform and may not always be possible if the training data is large and/or the model is complicate. Consistent with the present disclosure, an "offline" training is used where the training phase is performed separately from the prediction phase. The learned model trained offline is saved and reused for analyzing images.

Model training device 202 may be implemented with hardware specially programmed by software that performs the training process. For example, model training device 202 may include a processor and a non-transitory computer-readable medium (discussed in detail in connection with FIG. 3). The processor may conduct the training by performing instructions of a training process stored in the computer-readable medium. Model training device 202 may additionally include input and output interfaces to communicate with training database 201, network 206, and/or a user interface (not shown). The user interface may be used for selecting sets of training data, adjusting one or more parameters of the training process, selecting or modifying a framework of the learning model, and/or manually or semi-automatically providing prediction results associated with an image for training.

Consistent with some embodiments, the trained diagnosis model may be used by image processing device to analyze new biomedical images for diagnosis purpose. Image processing device 203 may receive one or more diagnosis models, e.g., networks 500, 600, 800, 1000, or 1200 that will be described in detail later, from model training device 202. Image processing device 203 may include a processor and a non-transitory computer-readable medium (discussed in detail in connection with FIG. 3). The processor may perform instructions of a medical diagnostic image analysis program stored in the medium. Image processing device 203 may additionally include input and output interfaces (discussed in detail in connection with FIG. 3) to communicate with biomedical image database 204, network 206, and/or a user interface (not shown). The user interface may be used for selecting biomedical images for analysis, initiating the analysis process, displaying the diagnostic results.

Image processing device 203 may communicate with biomedical image database 204 to receive biomedical images. In some embodiments, the biomedical images stored in biomedical image database 204 may include 3D images (e.g., 3D lung CT images) from one or more underlying subjects (e.g., patients susceptible to COVID-19). The biomedical images may be acquired by image acquisition devices 205. Image processing device 203 may perform an initial segmentation on the images. For example, a 3D lung ROI may be extracted by segmenting the 3D lung image. In some embodiments of the present disclosure, image processing device 203 may perform a COVID-19 detection (e.g., through applying a COVID-19 detection network on the 3D lung ROI) to determine a condition of the lung. For example, image processing device 203 may generate a probability score for the condition based on the 3D lung ROI. Image processing device 203 may further generate a heatmap for the 3D lung ROI and provide a diagnostic result based on the probability score for the underlying subject.

Figure 3:
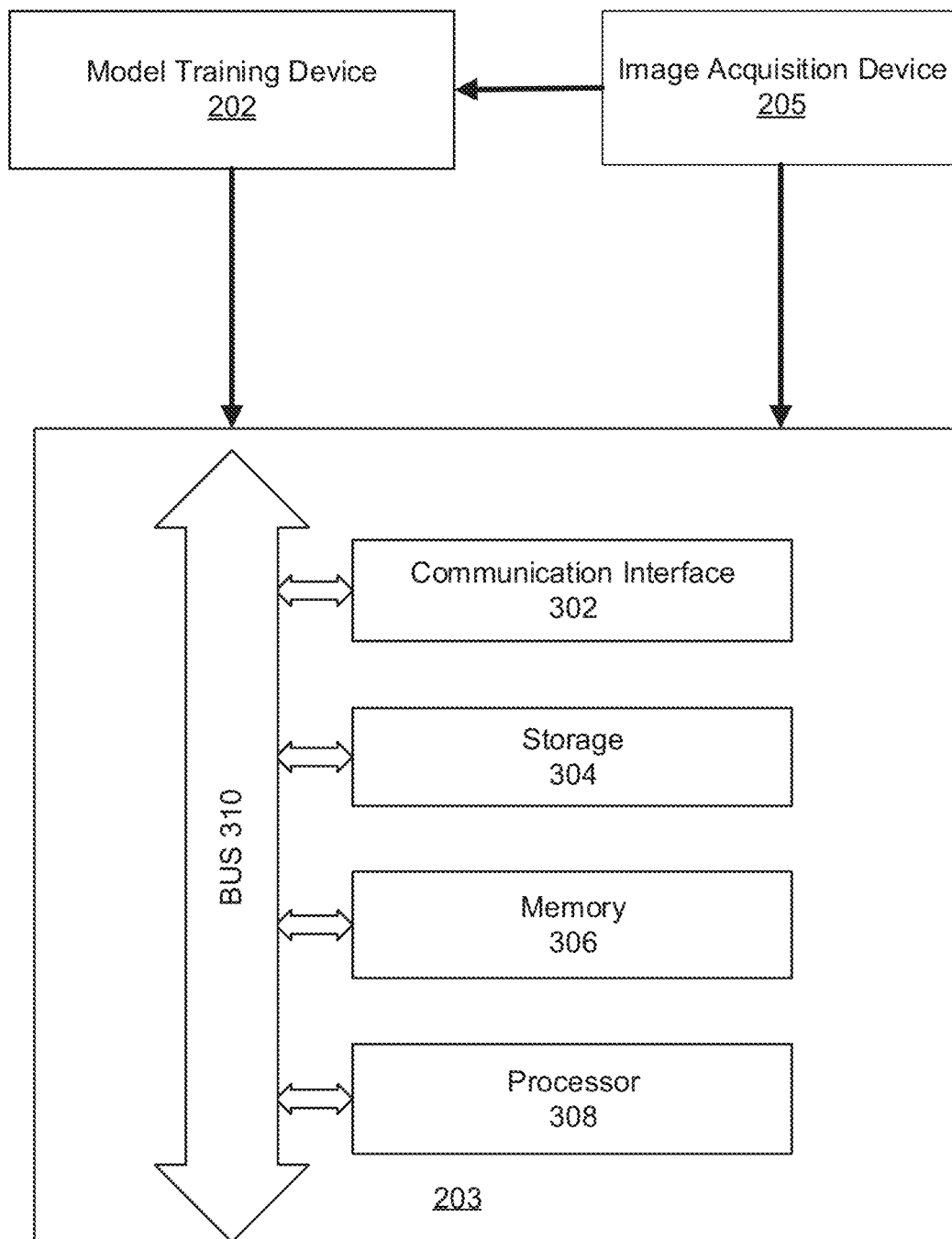
FIG. 3 illustrates a schematic diagram of an exemplary image processing device, according to certain embodiments of the disclosure.

Systems and methods of the present disclosure may be implemented using a computer system, such as shown in FIG. 3. In some embodiments, image processing device 203 may be a dedicated device or a general-purpose device. For example, the image processing device 203 may be a computer customized for a hospital for processing image data acquisition and image data processing tasks, or a server in a cloud environment. The image processing device 203 may include one or more processor(s) 308, one or more storage device(s) 304, and one or more memory device(s) 306. Processor(s) 308, storage device(s) 304, and memory device(s) 306 may be configured in a centralized or a distributed manner. Image processing device 203 may also include a biomedical image database (optionally stored in storage device 304 or in a remote storage), an input/output device (not shown, but which may include a touch screen, keyboard, mouse, speakers/microphone, or the like), a network interface such as communication interface 302, a display (not shown, but which may be a cathode ray tube (CRT) or liquid crystal display (LCD) or the like), and other accessories or peripheral devices. The various elements of image processing device 203 may be connected by a bus 310, which may be a physical and/or logical bus in a computing device or among computing devices.

Processor 308 may be a processing device that includes one or more general processing devices, such as a microprocessor, a central processing unit (CPU), a graphics processing unit (GPU), and the like. More specifically, processor 308 may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. Processor 308 may also be one or more dedicated processing devices such as application specific integrated circuits (ASICs), field programmable gate arrays (FPGAs), digital signal processors (DSPs), system-on-chip (SoCs), and the like.

Processor 308 may be communicatively coupled to storage device 304/memory device 306 and configured to execute computer-executable instructions stored therein. For example, as illustrated in FIG. 3, bus 310 may be used, although a logical or physical star or ring topology would be examples of other acceptable communication topologies. Storage device 304/memory device 306 may include a read only memory (ROM), a flash memory, random access memory (RAM), a static memory, a volatile or non-volatile, magnetic, semiconductor, tape, optical, removable, nonremovable, or other type of storage device or tangible (e.g., non-transitory) computer readable medium. In some embodiments, storage device 304 may store computer-executable instructions of one or more processing programs, learning networks used for the processing (e.g., networks 500, 600, 800, 1000, and/or 1200), and data (e.g., lung ROIs and feature maps) generated when a computer program is executed. The lung ROIs or the feature maps may be read from storage device 304 one by one or simultaneously and stored in memory device 306. Processor 308 may execute the processing program to implement each step of the methods described below. Processor 308 may also send/receive medical data to/from storage device 304/memory device 306 via bus 310.

Image processing device 203 may also include one or more digital and/or analog communication (input/output) devices, not illustrated in FIG. 3. For example, the input/output device may include a keyboard and a mouse or trackball that allow a user to provide input. Image processing device 203 may further include a network interface, illustrated as communication interface 302, such as a network adapter, a cable connector, a serial connector, a USB connector, a parallel connector, a high-speed data transmission adapter such as optical fiber, USB 3.0, lightning, a wireless network adapter such as a WiFi adapter, or a telecommunication (3G, 4G/LTE, etc.) adapter and the like. Image processing device 203 may be connected to a network through the network interface. Image processing device 203 may further include a display, as mentioned above. In some embodiments, the display may be any display device suitable for displaying a medical image and its diagnostic results. For example, the image display may be an LCD, a CRT, or an LED display.

Image processing device 203 may be connected to model training device 202 and image acquisition device 205 as discussed above with reference to FIG. 2. Other implementations are also possible.

Figure 4:
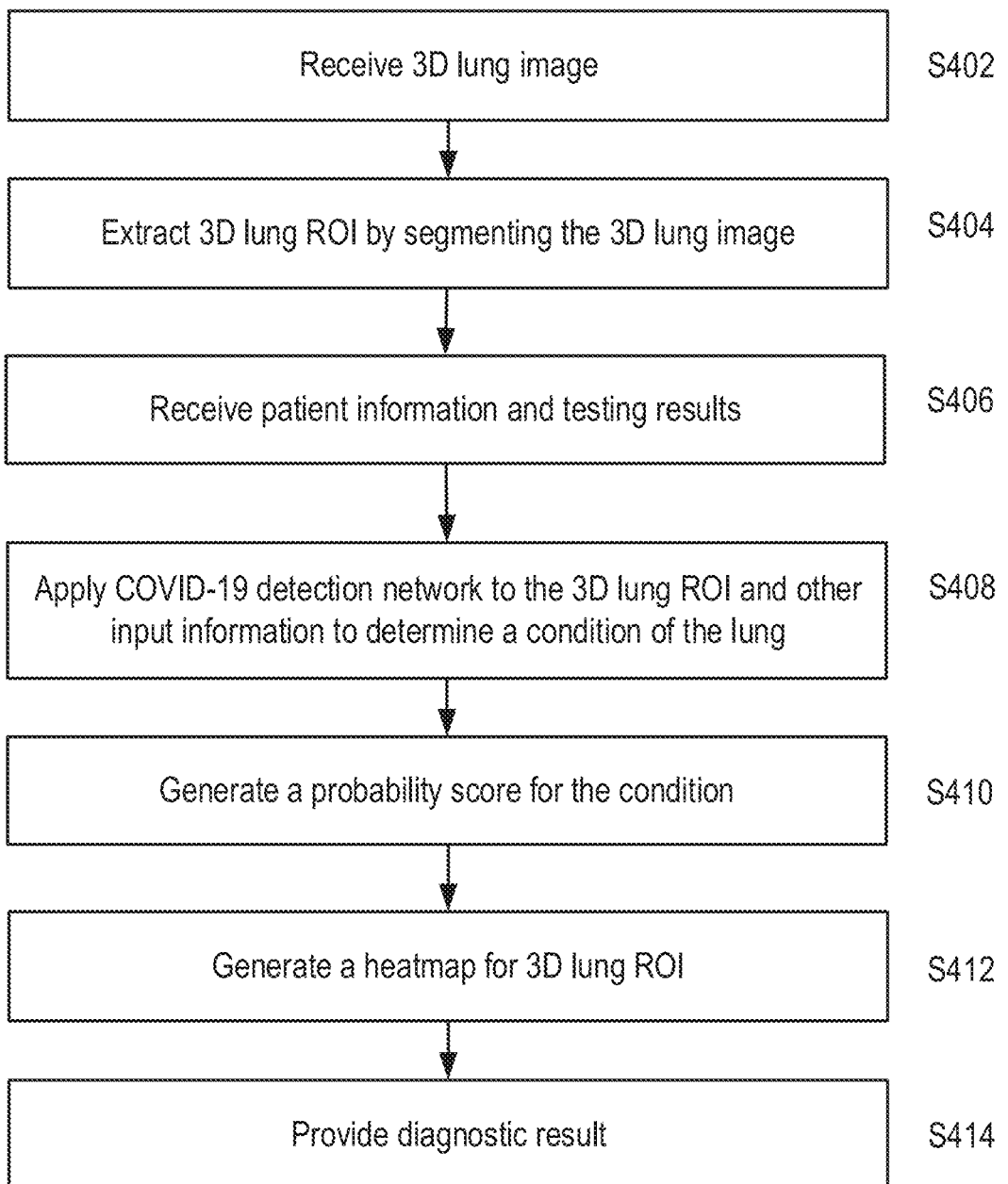
FIG. 4 is a flowchart of an exemplary method for detecting COVID-19, according to certain embodiments of the disclosure.

FIG. 4 is a flowchart of an exemplary method 400 for detecting COVID-19, according to embodiments of the disclosure. As shown in FIG. 4, method 400 may begin, at step S402, with receiving unannotated biomedical images, such as a 3D lung image of a single patient. The method may further include, at step S404, extracting 3D lung ROI by segmenting the received 3D lung image. For example, processor 308 may execute an FCN based method to automatically analyze the received image and segment the 3D lung image. The 3D lung ROI includes the lung from the 3D lung CT image. In some embodiments, the 3D lung ROI may be extracted semi-automatically. For example, a user may provide an annotation mask or a bounding box of the lung within the 3D lung image. Processor 308 then may apply the FCN based segmentation (e.g., U-Net 17) on the annotated 3D lung image. In some alternative embodiments, the user may manually segment the received 3D lung image to extract the 3D lung ROI. The extracted 3D lung ROI may then be stored in storage device 304.

As explained by way of example in the above-referenced provisional application, for ROI extraction, when a given input is a 3D lung image, an initial lung segmentation can be generated using an FCN based method as the ROI, which could be obtained automatically, semiautomatically, or manually.

Method 400 may also include, at step S406, receiving patient information and testing results. For example, communication interface 302 of image processing device 203 may receive one or more demographics of the patient, such as age and sex. Communication interface 302 may further receive a disease history of the patient, such as diabetes, hypertension, and previous cardiac events. Communication interface 302 may also receive the laboratory testing results of the patient, such as blood tests, lung function tests, pCO2 level, heart rate, blood pressure, and other physiologic measures. The above-mentioned patient information and testing results may be stored as meta data associated with each 3D lung image in biomedical image database 204 or in a separate medical database.

Figure 5:
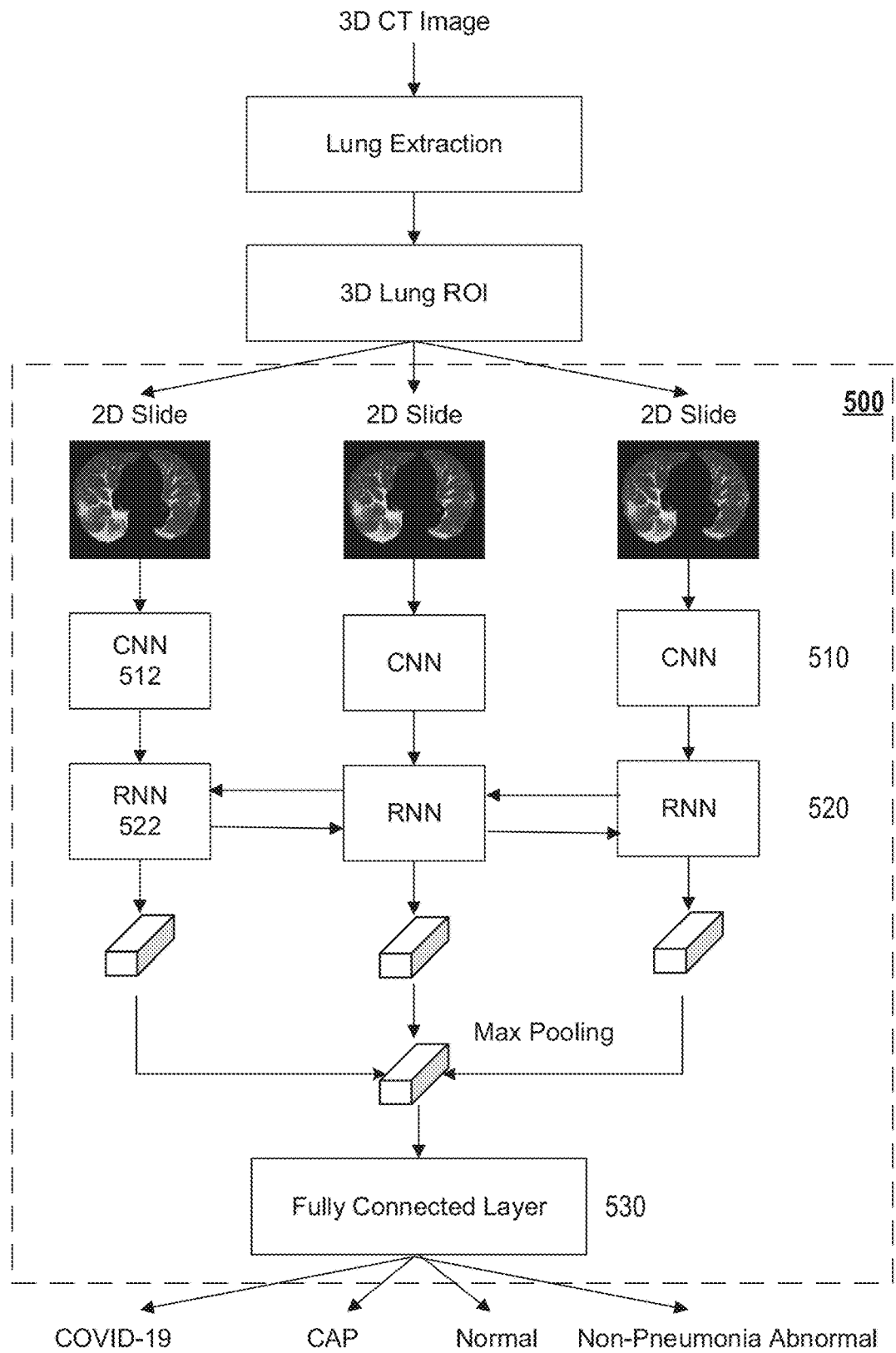
FIG. 5 illustrates an exemplary COVID-19 detection network applied by image processing device, according to certain embodiments of the present disclosure.

Method 400 may additionally include, at step S408, applying a COVID-19 detection network to the 3D lung ROI and other input information to determine a condition of the lung. For example, FIG. 5 illustrates a schematic overview of an exemplary COVID-19 detection network 500 (also referred to as "network 500") for detecting COVID-19 applied by image processing device 203, according to certain embodiments of the present disclosure. Network 500 may be trained using model training device 202. In some embodiments, network 500 may be trained by model training device 202 using any suitable gradient-based methods (e.g. Stochastic Gradient Descent, SGD) to optimize a classification loss function (e.g., cross-entropy loss, Area Under Curve (AUC) loss, etc.) for all parameters over a training dataset. The parameters of network 500 can be optimized by minimizing the loss function with ground truth outputs and the predicted values.

Network 500 may be designed to receive a 3D lung ROI as an input and output a label of the lung condition, as shown in FIG. 5. Network 500 may further receive patient information and testing results (not shown). In some embodiments, network 500 may be a multi-class classification learning network that labels the input 3D lung ROI as one of COVID-19, non-COVID-19 pneumonia, non-pneumonia abnormal (e.g., lung tumor, tuberculosis, cavitation, pleural effusion, or lymphadenopathy), or normal, in other words, network 500 may be an end-to-end learning model from a 3D lung ROI (with the patient information and testing results) to a disease type prediction (e.g., COVID-19, CAP, non-pneumonia abnormal, or normal). In some embodiments, non-COVID-19 pneumonia conditions can be further divided into other subgroups and associated with sub-labels. For example, the subgroup can include viral pneumonia, bacterial pneumonia, or the combination of these two. Network 500 can be used directly to predict the disease type in a single forward pass.

As explained by way of example in the above-referenced provisional application, a 3D deep learning framework can be used for the detection of COVID-19. The 3D deep learning framework for the detection of COVID-19 can extract both 2D local and 3D global representative features. The framework can include a CNN-RNN structure as the backbone, which takes a series of 3D image slices as input and generates features for the corresponding slices. The extracted features from all slices can then be combined by a max-pooling operation. The final feature map can be fed to a fully connected layer and the softmax activation function to generate a probability score for COVID-19 and other disease conditions. Alternatively, a 3D network could be used, in which a 3D CNN is used to extract the features instead of the CNN-RNN structure. In this example, the output types can include COVID-19, community-acquired pneumonia (CAP), and normal lung conditions and non-pneumonia-abnormal conditions. The framework can be used directly to predict the disease category in a single forward pass.

As shown in FIG. 5, network 500 can be constructed to include a convolutional neural network (CNN) layer 510, a recurrent neural network (RNN) layer 520, and a fully connected layer 530. In some embodiments, CNN layer 510 and the RNN layer 520 may process the 2D slices of the 3D lung ROI in parallel and fully connected layer 530 may then aggregate the processed results and generate the classification label. FIG. 5 shows an example where a plurality of 2D slices of the 3D lung ROI are input to network 500. In some embodiments, network 500 may include parallel CNN units (e.g., CNN 512) followed by respective RNN units (e.g., RNN 522). The 2D slices may be fed to a corresponding CNN unit (e.g., CNN 512) of the CNN layer. Each CNN unit acts as an encoder to learn and encode the 2D slice to learn local and spatial information and produce a vector of features in a fixed length (not shown).

The vector is then fed into the corresponding RNN unit (e.g., RNN 522) of the RNN layer. In some embodiments, the RNN layer may be a bidirectional RNN layer that includes a forward RNN layer and a reverse RNN layer to simultaneously learn a correlation in the key positive and negative directions of the sequence data. For example, the forward RNN layer and the reverse RNN layer are designed for extracting contextual information between the adjacent 2D slices and/or global features across the plurality of 2D slices. Because the 2D slices stack to form the third dimension of the 3D image, the 2D slices contain the structural correlations in that third dimension. In some embodiments, the forward RNN layer and the reverse RNN layer of the bidirectional RNN layer are not connected by edges, and can be separately trained by the general RNN training method. In some embodiments, computations of the forward RNN layer and the reverse RNN layer of the bidirectional RNN layer can be performed in parallel, which helps to improve computational efficiency. In various different embodiments, each RNN unit may use long short-term memory (LSTM) recurrent neural network, gate recurrent unit (GRU), convolutional GRU, convolutional LSTM recurrent neural network, and the like.

In some embodiments, each RNN unit of network 500 generates a feature map in a fixed length. The generated feature maps from all 2D slices are then combined by a max-pooling operation to form a composite feature map. Although the max-pooling operation is used as an example, other up-sampling layers, such as an average pooling operation, etc., may also be employed. Subsequently, the up-sampled data using the max-pooling operation is fed to fully connected layer 530 to determine a disease type (e.g., COVID-19, CAP, non-pneumonia abnormal, or normal) associated with the lung.

Figure 6:
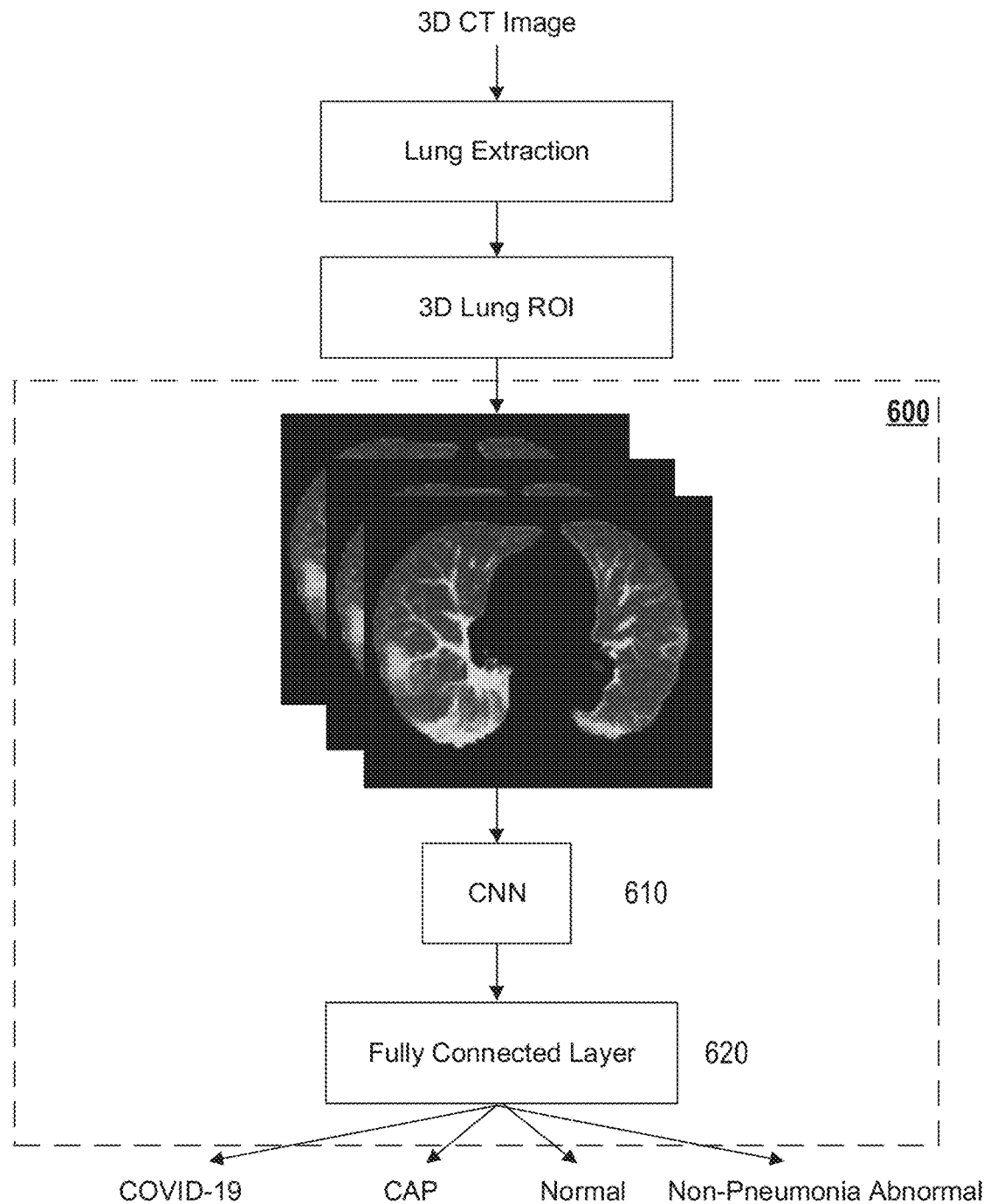
FIG. 6 illustrates another exemplary COVID-19 detection network applied by image processing device, according to certain embodiments of the present disclosure.

In some alternative embodiments, the COVID-19 detection network can be a 3D learning network that apply a 3D CNN on the 3D lung ROI directly. In some embodiments, the COVID-19 detection network may additionally take the patient information and/or testing results as input. For example, FIG. 6 illustrates another exemplary COVID-19 detection network 600 (also referred to as "network 600") applied by image processing device 203, according to certain embodiments of the present disclosure. Network 600 may be generated using model training device 202. In some embodiments, network 600 may be trained by model training device 202 using any suitable gradient-based methods (e.g. SGD) to optimize a classification loss function (e.g., cross-entropy loss, Area Under Curve loss, etc.) for all parameters over a training dataset. The parameters of network 600 can be optimized by minimizing the loss function with ground truth outputs and the predicted values.

Network 600 may receive a 3D lung ROI as an input and output label of the lung condition, as shown in FIG. 6. Network 600 may further receive patient information and testing results (not shown). Consistent with some embodiments, like network 500, network 600 may be a multi-class classification learning network that labels the input 3D lung ROI as one of COVID-19, non-COVID-19 pneumonia, non-pneumonia abnormal, or normal. In other words, network 600 may be an end-to-end learning model from a 3D lung ROI (with the patient information and testing results) to a disease type prediction (e.g., COVID-19, CAP, non-pneumonia abnormal, or normal). Network 600 can be used directly to predict the disease type in a single forward pass.

As shown in FIG. 6, network 600 can be constructed to include a 3D CNN 610 and a fully connected layer 620. In one example, a 3D lung ROI is input to network 600. The 3D lung ROI may be fed to 3D CNN 610, which acts as an encoder to learn and encode the 3D lung ROI to learn local and spatial information and produce a feature map (not shown). Subsequently, the produced feature map from the 3D lung ROI is fed to fully connected layer 620 to determine a disease type (e.g., COVID-19, CAP, non-pneumonia abnormal, or normal) associated with the lung.

Returning to FIG. 4, at step S410, a probability score for the condition is generated. For example, the produced feature map from the 3D lung ROI by CNN layer 510 and RNN layer 520 of network 500 or 3D CNN 610 of network 600 may be fed to the fully connected layer (e.g., fully connected layer 530 of network 500 or fully connected layer 620 of network 600) and a softmax activation function (not shown) to generate a probability score for each disease type (e.g., COVID-19, CAP, non-pneumonia abnormal, or normal). In some embodiments, the disease type having a highest probability score among all the disease types may be assigned as the condition of the lung. For example, the condition of the lung may be labeled as COVID-19 if the probability score for COVID-19 is higher than other probability scores for other conditions.

In some embodiments, to provide a visual evidence for the decision making, a heatmap for the 3D lung ROI may be generated at step S412. For example, in the heatmap, a red color may highlight an activation region associated with the predicted disease type. At step S414, method 400 may further include providing a diagnostic output based on the processing of the 3D lung image and the disease prediction. In some embodiments, the diagnostic output may include the probability score for each disease type, the predicted disease type, the generated heatmap, and the like. In some embodiments, method 400 may additionally output certain medical data, such as the 3D lung image, the 3D lung ROI, the 2D slices, the patient information, the testing results, and the like. The diagnostic output and the medical data may be displayed on a display of image processing device 203.

Figure 7:
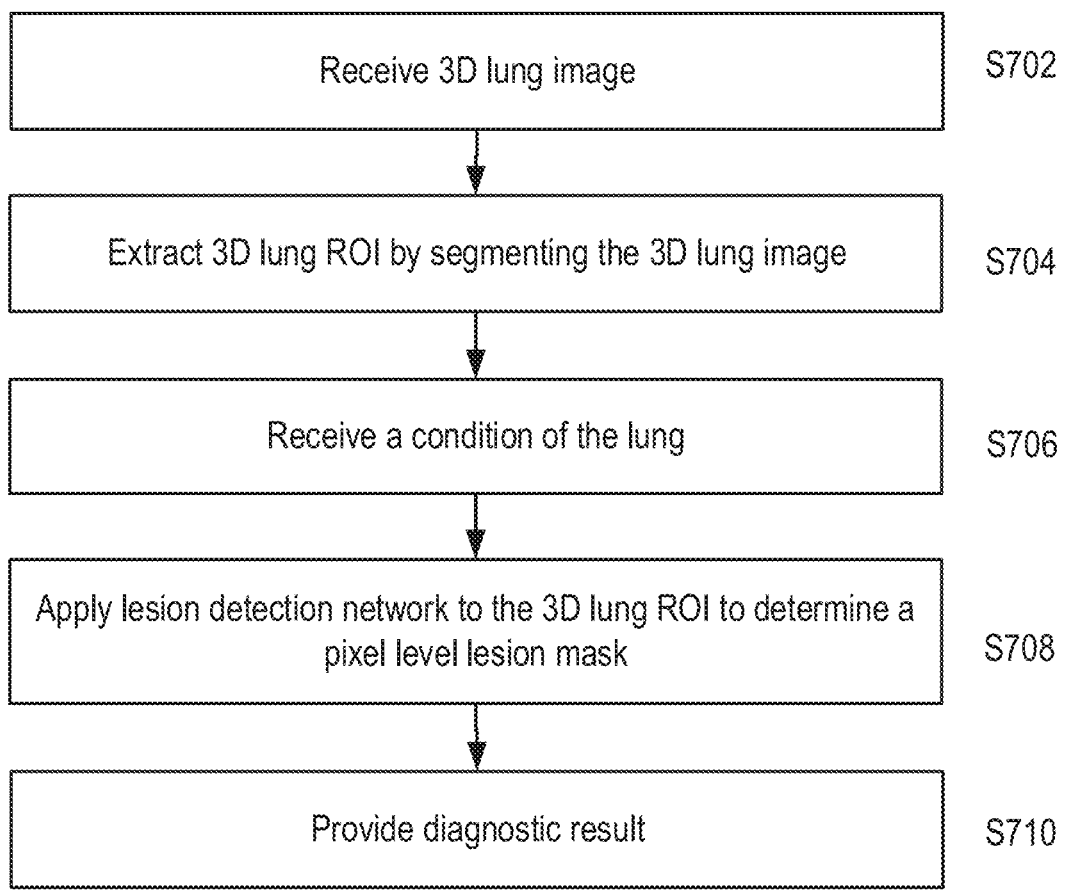
FIG. 7 is a flowchart of an exemplary method for predicting a lesion mask, according to certain embodiments of the disclosure.

FIG. 7 is a flowchart of an exemplary method 700 for predicting a lesion mask, according to certain embodiments of the disclosure. As shown in FIG. 7, method 700 may begin, at step S702, with receiving unannotated biomedical images, such as a 3D lung image of a single patient. Method 700 may further include, at step S704, extracting 3D lung ROI by segmenting the received 3D lung image. For example, processor 308 may execute the above-mentioned FCN based method to automatically analyze the received image and segment the 3D lung image. Consistent with some embodiments, the 3D lung ROI may be extracted semi-automatically. For example, the user may provide an annotation mask or a bounding box of the lung within the 3D lung image. Processor 308 may then apply the FCN based segmentation (e.g., U-Net 17) on the annotated 3D lung image. In some alternative embodiments, the user may manually segment the received 3D lung image to extract the 3D lung ROI. The extracted 3D lung ROI may then be stored in storage device 304.

Method 700 may also include, at step S706, receiving a condition of the lung. In some embodiments, the condition of the lung may be provided by the user. In some alternative embodiments, the condition of the lung may be predicted using the COVID-19 detection network (e.g., network 500 or network 600) based on the 3D lung image. For example, the condition of the lung may be one of COVID-19, CAP, non-pneumonia abnormal, or normal. It is contemplated that the lung can be in other conditions that not limited to the above-mentioned disease categories.

Method 700 may additionally include, at step S708, applying lesion detection network to the 3D lung ROI to determine a pixel level lesion mask. Consistent with the present disclosure, a pixel level lesion mask includes a binary label for each pixel that indicates whether the pixel corresponds to a lesion or a non-lesion. For example, the pixel level lesion mask may be a black and white image that is the same size as the 3D lung ROI image. In some embodiments, when an annotation of the lesion is available for training a detection and segmentation model, a supervised approach may be used for detecting and segmenting lesions. In some embodiments, when no or fewer annotation data are available, unsupervised, semi-supervised, or weakly supervised methods can be used for training a model for detecting and segmenting the lesions.

Figure 8:
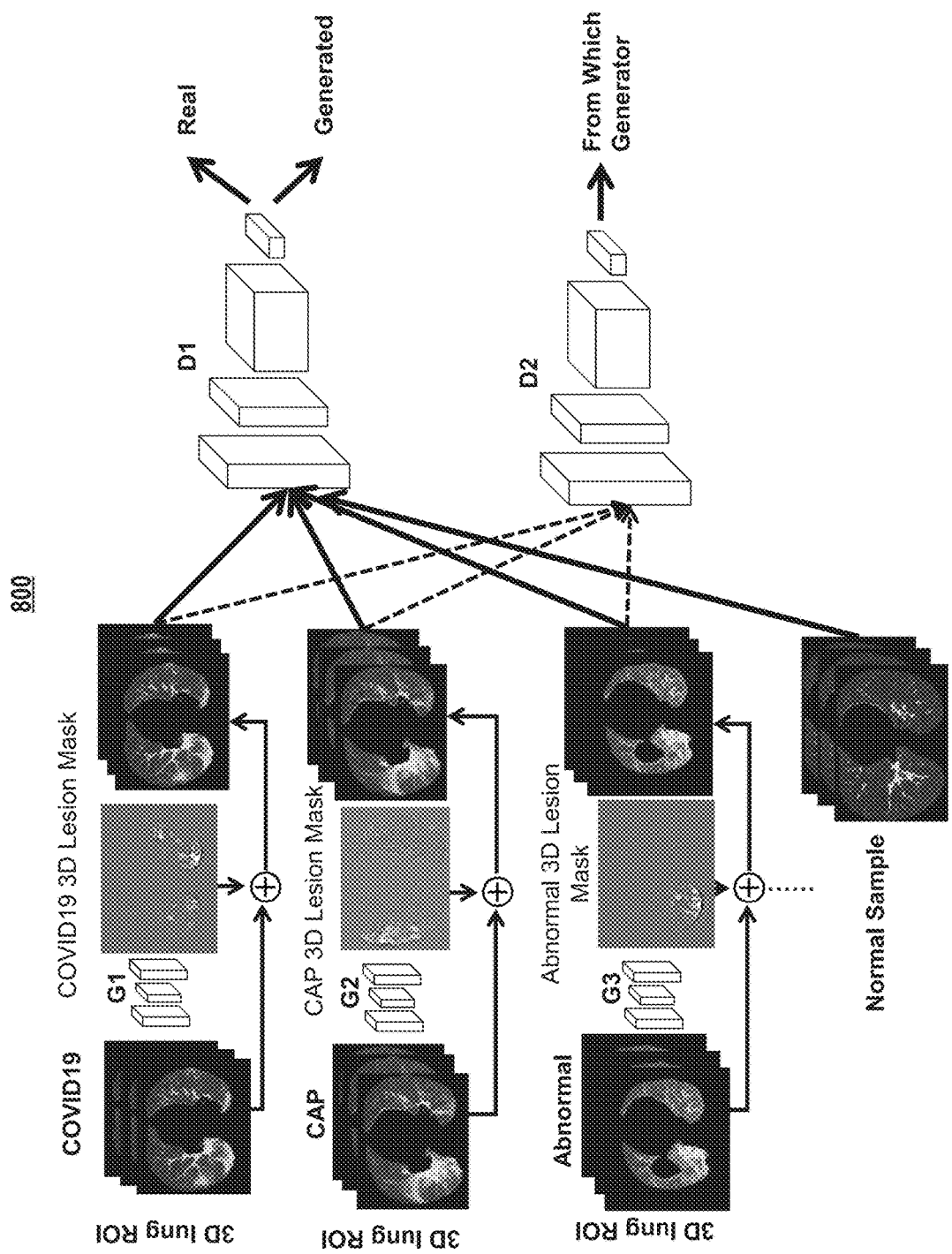
FIG. 8 illustrates an exemplary lesion detection network applied by image processing device, according to certain embodiments of the present disclosure.

For example, FIG. 8 illustrates an exemplary lesion detection network 800 (also referred to as "network 800") for detecting and segmenting lesions performed by image processing device 203, according to certain embodiments of the present disclosure. In some embodiments, network 800 may be an unsupervised lesion detection model based on a generative adversarial network (GAN). As shown in FIG. 8, network 800 includes three lesion mask generators (e.g., G1, G2, and G3) and two discriminators (e.g., D1 and D2). Each lesion mask generator may receive an input of a corresponding 3D lung ROI and generate a 3D lesion mask. A respective generator of network 800 may be selected for use based on the type of the lung condition diagnosed in the 3D lung ROI. For example, a 3D lung ROI labeled as having a COVID-19 condition may be fed to generator G1. Generator G1 may then produce a COVID-19 3D lesion mask for the received COVID-19 3D lung ROI in a single forward pass. Similarly, a 3D lung ROI labeled as having a CAP condition may be fed to generator G2. Generator G2 may then produce a CAP 3D lesion mask for the received CAP 3D lung ROI in the single forward pass. A 3D lung ROI labeled as abnormal may be fed to generator G3. Generator G3 may then produce an abnormal 3D lesion mask for the received abnormal 3D lung ROI in the single forward pass.

As shown in FIG. 8, during training, generators G1, G2, and G3 may be trained jointly as part of network 800. Sample images used for training network 800 may include images of all types of lung conditions, e.g., COVID-19, CAP, non-pneumonia abnormal, and normal conditioned images. During training, the COVID-19 3D lesion mask generated by generator G1 is applied to the COVID-19 3D lung ROI to produce a generated COVID-19 3D lung ROI. Similarly, the CAP 3D lesion mask generated by generator G2 is applied to the CAP 3D lung ROI to produce a generated CAP 3D lung ROI. The abnormal 3D lesion mask generated by generator G3 is applied to the abnormal 3D lung ROI to produce a generated abnormal 3D lung ROI. The generated 3D lung ROIs (including the generated COVID-19 3D lung ROI, the generated CAP 3D lung ROI, and the generated abnormal 3D lung ROI) and the original 3D lung ROIs (extracted from the 3D lung images) may be fed to discriminator D1. In some embodiments, additionally, normal 3D lung ROIs are also fed to discriminator D1. In some embodiments, discriminator D1 is a binary classifier aiming to classify the original 3D lung ROIs and the generated 3D lung ROIs. In some embodiments, discriminator D2 is a multi-classifier aiming to predict a corresponding generator associated with each generated 3D lung ROI.

In some embodiments model training device 202 may jointly optimize the generators and the discriminators using any suitable gradient-based methods (e.g. SGD). For example, model training device 202 may use one or more GAN loss functions or structures to optimize network 800, such as Wasserstein GAN (WGAN) loss, Deep Convolutional GAN (DCGAN) loss, etc. In some embodiments, generators G1-G3 and discriminators D1-D2 in network 800 may be implemented as CNNs. It is contemplated that generators G1-G3 and discriminators D1-D2 are not limited to any specific network structures. For example, generators G1-G3 can be implemented as any suitable type of segmentation networks. Discriminators D1-D2 can be implemented as any suitable types of classification networks.

Returning to FIG. 7, at step S710, method 700 may also include providing a diagnostic output based on the processing of the 3D lung image and the determined pixel level lesion mask. In some embodiments, the diagnostic output may further include the output of network 800, such as the 3D pixel level lesion mask, the lesion related information (e.g., location, quantity, and volume/size). In some embodiments, the diagnostic output may additionally include the input of the medical data, such as 3D lung image, the 3D lung ROI, the disease type, and the like.

Although the disclosure of network 800 is made using a COVID-19 related lesion detection and segmentation model as an example, the disclosed embodiments may be adapted and implemented to other types of lesion segmentation system that detects and segments lesions of other types of disease related to unrelated to lung. For example, the embodiments may be readily adapted for detecting and segmenting an intracerebral hemorrhage (ICH) from a 3D head scan medical image.

Figure 9:
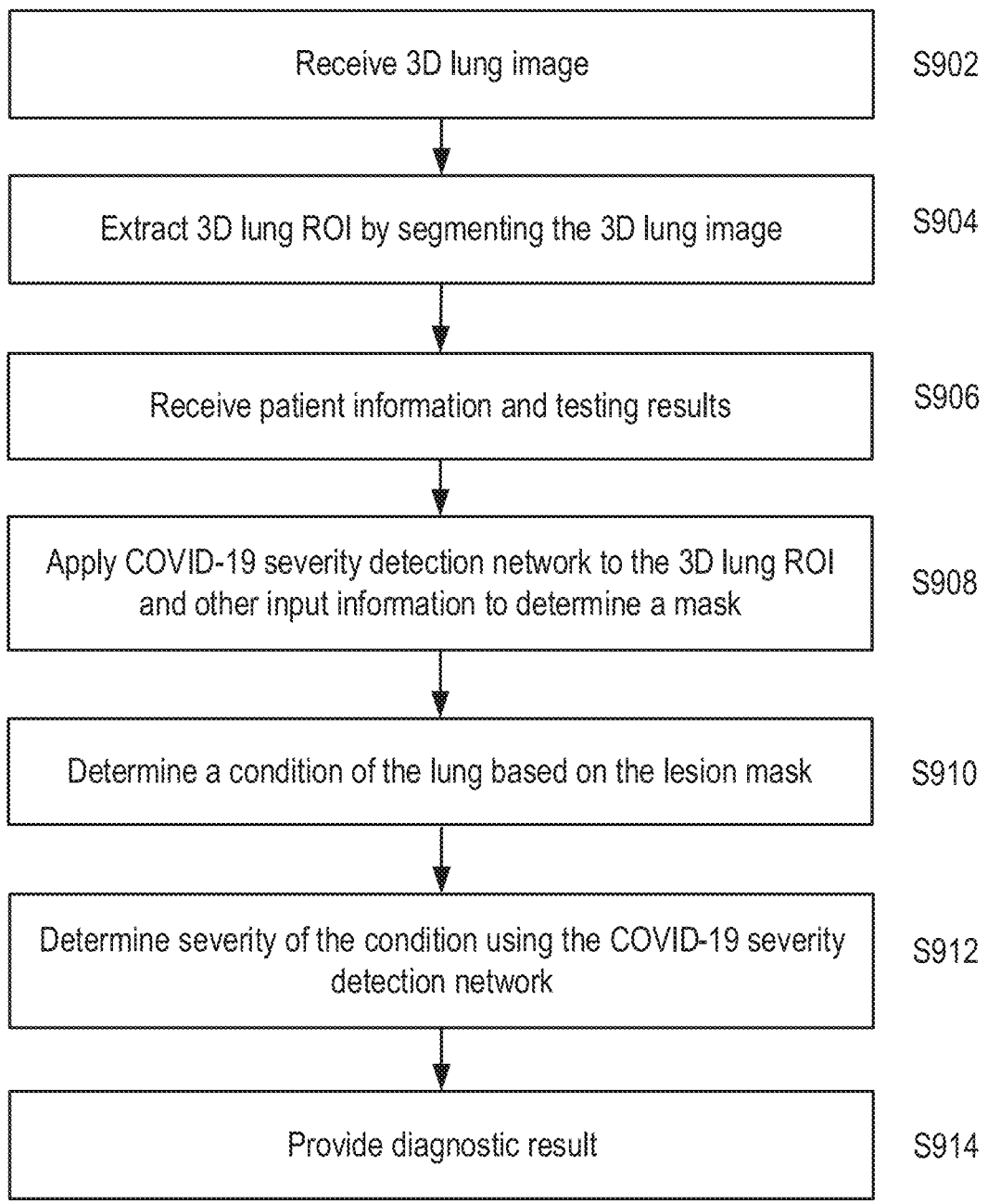
FIG. 9 is a flowchart of an exemplary method for determining a severity of a condition of a lung, according to certain embodiments of the disclosure.

FIG. 9 is a flowchart of an exemplary method 900 for determining a severity of a condition of a lung, according to certain embodiments of the disclosure. As shown in FIG. 9, method 900 may begin, at step S902, with receiving unannotated biomedical images, such as a 3D lung image of a single patient. The method may further include, at step S904, extracting a 3D lung ROI by segmenting the received 3D lung image. Consistent with some embodiments, processor 308 may execute the FCN based method to automatically analyze the received image and segment the 3D lung image. In some alternative embodiments, the 3D lung ROI may be extracted semi-automatically. For example, the user may provide an annotation mask or a bounding box of the lung within the 3D lung image. Processor 308 may then apply the FCN based segmentation (e.g., U-Net 17) on the annotated 3D lung image. In some alternative embodiments, the user may manually segment the received 3D lung image to extract the 3D lung ROI, The extracted 3D lung ROI may then be stored in storage device 304.

Method 900 may also include, at step S906, receiving patient information and testing results. Consistent with embodiments of the present disclosure, communication interface 302 of image processing device 203 may receive one or more demographics of the patient, such as age and sex. Communication interface 302 may further receive a disease history of the patient, such as diabetes, hypertension, previous cardiac events, etc. Communication interface 302 may also receive the laboratory testing result of the patient, such as blood tests, lung function tests, pCO2 level, heart rate, blood pressure, or other physiologic measures. Consistent with embodiments of the present disclosure, the above-mentioned patient information and testing results may be stored as meta data of each 3D lung image in biomedical image database 204 or in a separate medical database.

Figure 10:
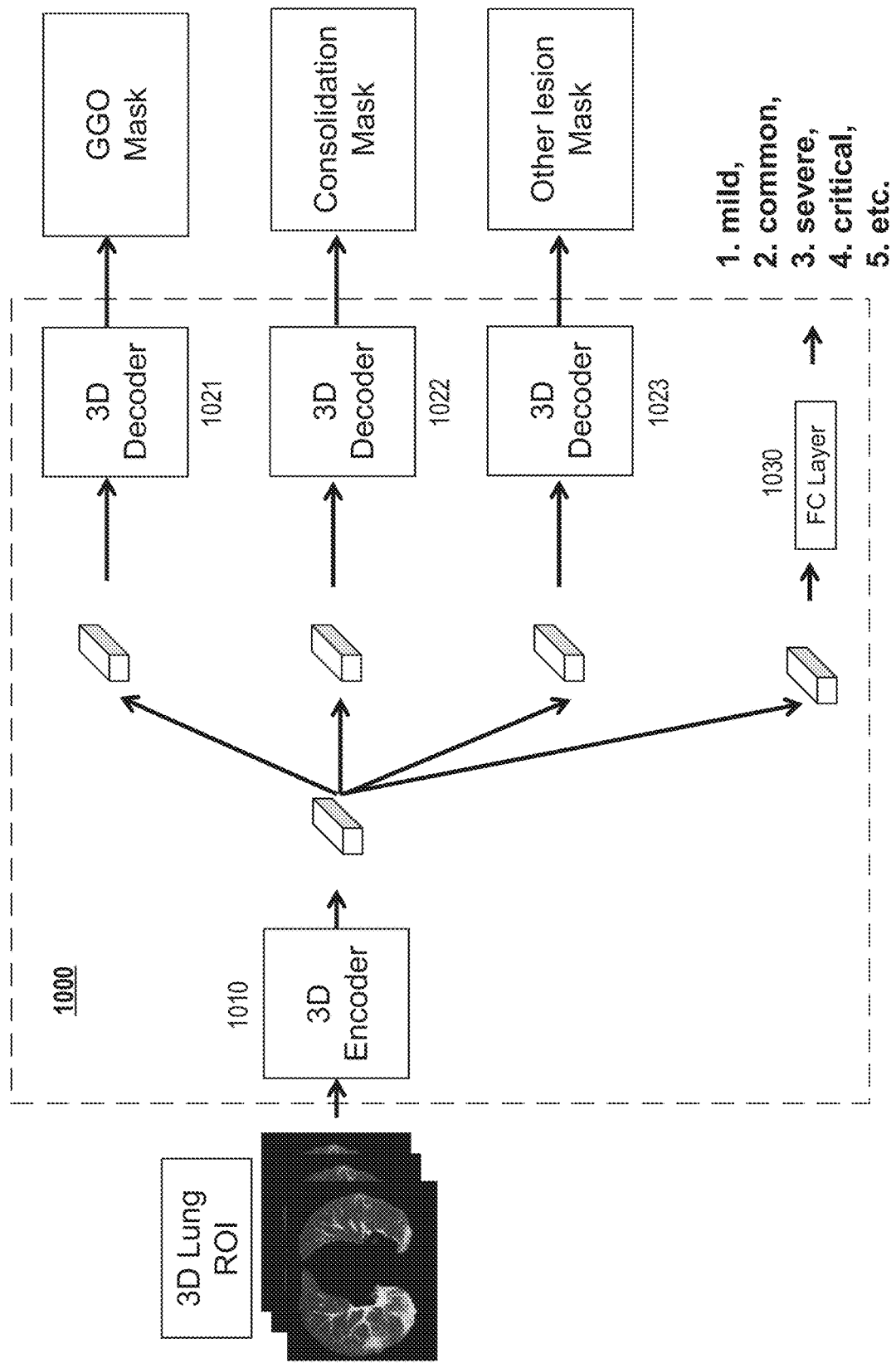
FIG. 10 illustrates an exemplary COVID-19 severity detection network applied by image processing device, according to certain embodiments of the present disclosure.

Method 900 may additionally include, at step S908, applying COVID-19 severity detection network to the 3D lung ROI and other input information to determine a mask of a lesion. For example, FIG. 10 illustrates an exemplary COVID-19 severity detection network 1000 (also referred to as "network 1000") performed by image processing device 203, according to certain embodiments of the present disclosure. In some embodiments, network 1000 may be a multi-task framework for disease(e.g., COVID-19) severity assessment. The input to network 1000 may be the 3D lung ROI image for each disease. Patient information including demography, disease history, laboratory testing results (e.g., bloods tests, lung function tests, pCO2 level, heart rate, blood pressure) could also be used as the input features to network 1000. In some embodiments, the output of network 1000 may include the 3D lesion for each disease and the disease severity assessment type. For example, the severity may be one of mild, common, severe, and critical, etc.

Network 1000 may be trained using model training device 202. In some embodiments, network 1000 may be trained by model training device 202 using any suitable gradient-based methods (e.g. SGD method) to jointly optimize a classification loss function (e.g., cross-entropy loss, AUC loss, etc.) for parameters in the severity classification task and a segmentation loss function for parameters in the mask segmentation task. The parameters of network 1000 can be jointly optimized by minimizing the loss functions with ground truth outputs and the predicted values.

As shown in FIG. 10, network 1000 can be constructed to include a 3D encoder 1010, a plurality of 3D decoders 1021-1023, and a fully connected (FC) layer 1030. In some embodiments, network 1000 may be an end-to-end learning model predicting a disease severity type prediction (e.g., mild, common, severe, critical, etc.) from a 3D lung ROI (with the patient information and testing results). That is, network 1000 can be used directly to predict the disease severity type in a single forward pass. As shown in FIG. 10, network 1000 may receive a 3D lung ROI as an input. In some embodiments, network 1000 may further receive patient information and testing results (not shown in FIG. 10). The 3D lung ROI and other input information may be fed to 3D encoder 1010 to encode local and spatial information of the 3D lung ROI into a feature map. The feature map is then fed into the plurality of 3D decoders for different lesion features. Each decoder produces a lesion mask for each type of lesion based on the 3D lung ROI. For example, as shown in FIG. 10, three 3D decoders 1021-1023 are used to detect different types of lesion, such as ground-glass opacity (GGO), consolidation, and other types. As a result, three lesion masks are produced by 3D decoders respectively. For example, 3D decoder 1021 produces a GGO mask, 3D decoder 1022 produces a consolidation mask, and 3D decoder 1023 produces an other lesion mask. In some embodiments, 3D encoder 1010 and 3D decoders 1021-1023 may be implemented in any suitable types of ITN networks.

Returning to FIG. 9, at step S910, method 900 further includes determining a condition of the lung based on the produced lesion masks. In some embodiments, the condition of the lung may be determined based on one or a combination of the lesion masks. In some embodiments, a probability score for each disease type of the lung may be generated based on the produced lesion masks. A disease type having a highest probability score among all the disease types may be assigned as the condition of the lung. For example, the condition of the lung may be labeled as COVID-19 if the probability score for COVID-19 is higher than other probability scores for the other disease types.

Method 900 may also include, at step S912, determining severity of the condition using network 1000. As shown in FIG. 10, the feature map is fed to FC layer 1030 and a softmax activation function (not shown) sequentially to generate a probability score for each disease severity type (e.g., mild, common, severity, critical, etc.). A disease severity type having a highest probability score among all the disease severity types may be assigned as the severity of the condition of the lung. That is, the severity determination branch of network 100 is a classifier that does a multi-class classification. For example, the severity of the condition of the lung may be labeled as mild if the probability score for mild is higher than other probability scores for the other severity types.

In some embodiments, model training device 202 may jointly train 3D encoder 1010, 3D decoders 1021-1023, and FC layer 1030 of network 1000. The decoders can be optimized using any suitable segmentation loss functions. In some embodiments, optimized 3D decoders 1021-1023 may be used to optimize 3D encoder 1010 and FC layer 1030 using the classification loss function.

Returning to FIG. 9, at step S914, method 900 may further include providing a diagnostic output based on the processing of the 3D lung image and the disease severity prediction. In some embodiments, the diagnostic output may include the output of network 1000, such as the lesion masks, the condition of the lung, the predicted disease severity type, and the like. In some embodiments, the diagnostic output may further include the input of the medical data, such as 3D lung image, the 3D lung ROI, the patient information, the testing results, and the like.

Although the disclosure of network 1000 is made using a COVID-19 severity prediction as an example, the disclosed embodiments may be adapted and implemented to predict severity type for other diseases. For example, the embodiments may be readily for predicting a severity type of an ICH based on 3D head scan medical image. An ICH severity prediction network can be trained to perform a lesion (e.g., bleeding region) mask segmentation and predict the severity of the ICH.

Figure 11:
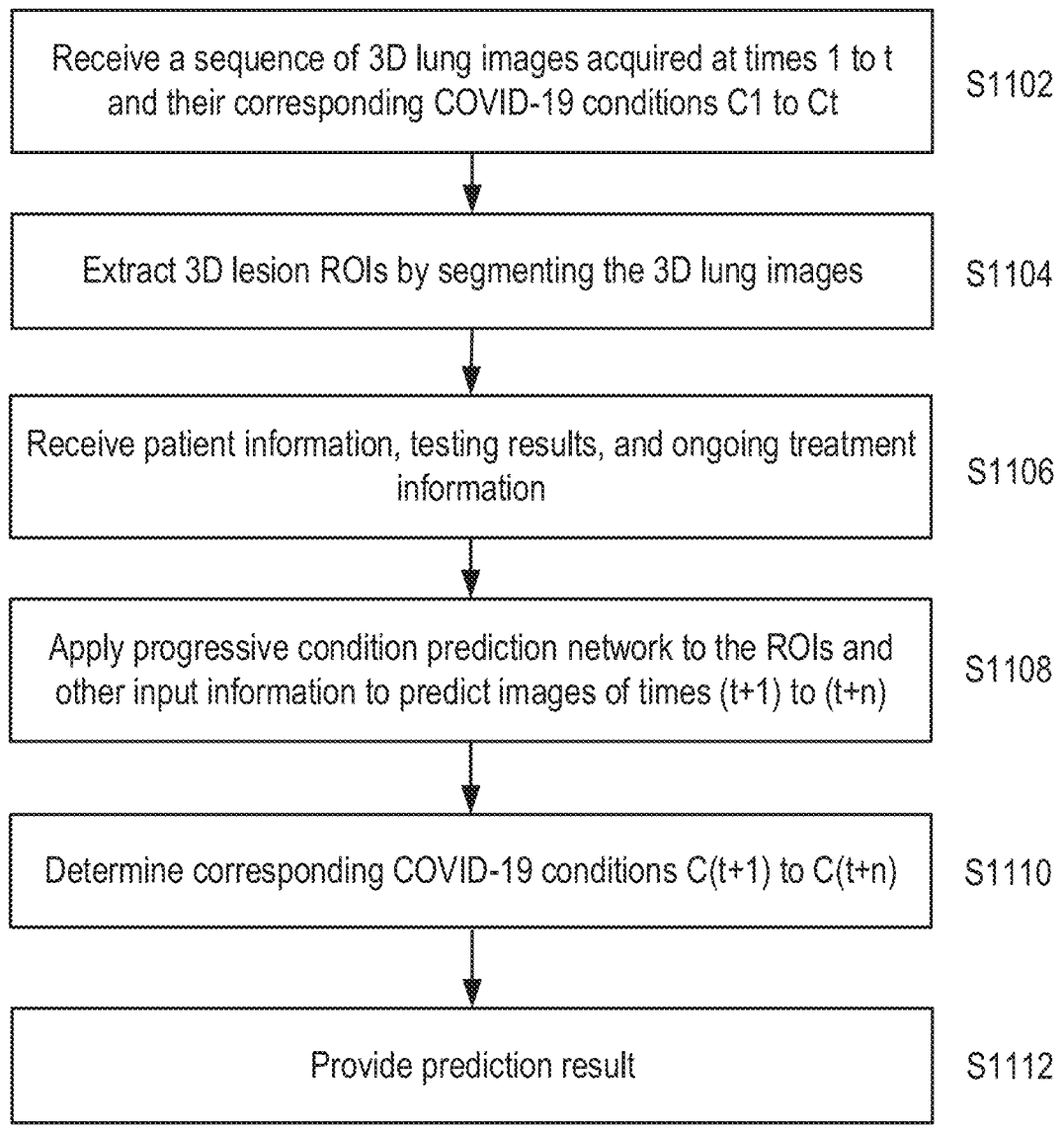
FIG. 11 is a flowchart of an exemplary method for predicting a COVID-19 follow-up condition and generating a predicted 3D lesion image, according to certain embodiments of the disclosure.

FIG. 11 is a flowchart of an exemplary method 1100 for predicting a COVID-19 follow-up condition and generating a predicted 3D lesion image, according to certain embodiments of the disclosure. As shown in FIG. 11, method 1100 may begin, at step S1102, with receiving a sequence of unannotated biomedical images and their corresponding COVID-19 conditions. The sequence of images may be acquired at a series different time points during the progression of a disease (e.g., COVID-19) and the disease has different conditions at these time points. For example, processor 308 may receive a sequence of 3D lung images of a patient acquired at times 1 to t, and their corresponding COVID-19 conditions $C_1$ to $C_t$, where t≥1.

Method 1100 may further include, at step S1104, extracting 3D lesion ROIs by segmenting the received 3D lung images. For example, processor 308 may execute a segmentation program to automatically segment the received 3D lung images as the 3D lesion ROIs. In some embodiments, the 3D lesion ROIs may be extracted semi-automatically. For example, a user may provide an annotation mask or a bounding box of the lesion within each 3D lung image. Processor 308 may then execute the segmentation program on the annotated 3D lung images. In some alternative embodiments, the user may manually segment each received 3D lung image to extract the 3D lesion ROI. In some embodiments, network 800 may be used to generate the 3D lesion ROIs (e.g., COVID-19 3D lesion masks) based on the received 3D lung images and the COVID-19 conditions. The extracted 3D lesion ROIs may then be stored in storage device 304.

Method 1100 may also include, at step S1106, receiving patient information, testing results, and ongoing treatment information. For example, communication interface 302 of image processing device 203 may receive one or more demographics of the patient, such as age, sex, height, weight, etc. Communication interface 302 may further receive a disease history of the patient, such as presence or absence of diabetes, hypertension, and previous cardiac events. Communication interface 302 may also receive laboratory testing results of the patient, such as blood tests, lung function tests, pCO2 level, heart rate, blood pressure, and other physiologic measures. Communication interface 302 may additionally receive information of an ongoing treatment, such as medications and drugs treatment. The above-mentioned patient information, testing results, and ongoing treatment information may be stored as meta, data of each 3D lung image in biomedical image database 204 or in a separate medical database.

Method 1100 may additionally include, at step S1108, applying progressive condition prediction network to the 3D lesion ROIs and other input information to predict conditions of future time points, such as t+1 to t−n, where n≥1. The conditions may include different levels, including, e.g., disease improvement, moderate disease progression, mild disease progression, severe disease progression, etc. In some embodiments, the conditions may be predicted by predicting 3D lesion images at these future tune points. The predicted conditions may be used by clinicians for disease progression evaluation. For example, FIG. 12 illustrates an exemplary progressive condition prediction network 1200 (also referred to "network 1200") performed by image processing device 203, according to certain embodiments of the present disclosure.

Figure 12:
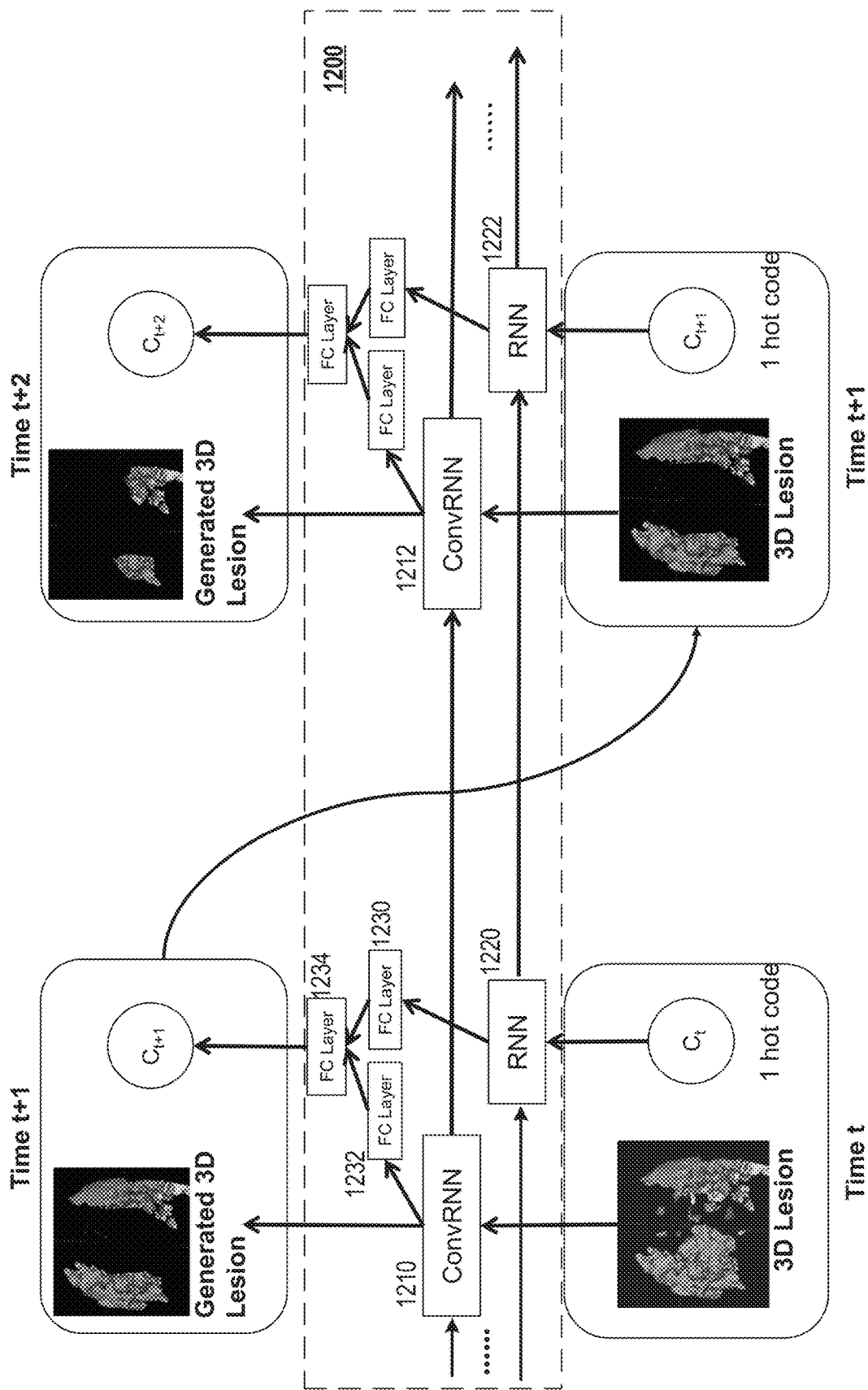
FIG. 12 illustrates an exemplary progressive condition prediction network applied by image processing device, according to certain embodiments of the present disclosure.

As shown in FIG. 12, network 1200 may be trained using model training device 202. In some embodiments, network 1200 may be trained by model training device 202 using any suitable gradient-based methods (e.g. SGD) to optimize a classification loss function (e.g., cross-entropy loss, AUC loss, etc.) for all parameters over a training dataset. The parameters of network 1200 can be optimized by minimizing the loss function with ground truth outputs and the predicted values. Network 1200 may receive a sequence of 3D lesion ROIs and the corresponding COVID-19 conditions as inputs. In some embodiments, network 1200 may further receive the patient information, the testing results, and the ongoing treatment information as additional inputs (not shown in FIG. 12).

As shown in FIG. 12, network 1200 can be constructed to include a forward convolutional RNN (ConvRNN) layer, a forward recurrent neural network (RNN) layer, and a plurality of FC layers. Using a 3D lesion ROI and the corresponding COVID-19 condition $C_t$ (implemented as a one-hot code) acquired at time t as an exemplary input to network 1200. The 3D lesion ROI may be fed to a corresponding ConvRNN unit 1210 of the ConvRNN layer. In some embodiments, each ConvRNN unit (e.g., ConvRNN unit 1210 or 1212) not only encodes the 3D lesion ROI to learn local and spatial information but also learns sequential information from earlier 3D lesion ROIs via an antecedent ConvRNN unit. For example, ConvRNN unit 1212 learns information from its antecedent ConvRNN unit 1210. In some embodiments, ConvRNN unit 1210 may produce a predicted 3D lesion ROI as a generated 3D lesion ROI at time t+1.

Returning to FIG. 11, at step S410, method 1100 may further include determining corresponding COVID-19 conditions $C_{t+1}$ to $C_{t+n}$. For example, as shown in FIG. 12, the COVID-19 condition $C_t$ at time t may be fed to a corresponding RNN unit (e.g., RNN unit 1220) of the forward RNN layer. In some embodiments, RNN unit 1220 may learn a correlation in the key positive direction of the sequence data (e.g., COVID-19 conditions $C_1$-$C_t$) using the forward RNN layer. RNN unit 1220 may generate a feature map (not shown) to feed a FC layer 1230 to generate a vector indicative of each COVID-19 condition (e.g., Yes, No). The output of ConvRNN unit 1210 may also be fed to another FC layer 1232 and generate another vector indicative of each COVID-19 condition. The two vectors may be fed to a third FC layer 1234 and generate a one-hot code $C_{t+1}$ indicative of COVID-19 condition at time t+1. In various embodiments, each RNN unit may use long short-term memory (LSTM) recurrent neural network, gate recurrent unit (GRU), convolutional GRU, convolutional LSTM recurrent neural network, and the like. Sequentially, the generated 3D lesion ROI and the COVID-19 condition $C_{t+1}$ may be fed to the following ConvRNN unit 1212 and RNN unit 1222 to produce a generated 3D lesion and a COVID-19 condition $C_{t+2}$ at time t+2. Accordingly, network 1200 can be used to predict COVID-19 follow-up conditions and generate predicted 3D lesion ROI images for the follow-up time steps (t+1) to (t+n) in a single forward pass.

Returning to FIG. 11, at step S1112, method 1100 may further include providing a diagnostic output based on the prediction of the COVID-19 follow-up conditions and the generation of the predicted 3D lesion ROI images. In some embodiments, the diagnostic output may include the output of the progressive condition prediction network, such as the COVID-19 follow-up conditions, the predicted 3D lesion ROI images for the follow-up time steps, and the like. In some embodiments, the diagnostic output may further include the input of the medical data, such as the sequence of the 3D lung images, the 3D lesion ROIs, the corresponding COVID-19 conditions, the patient information, the testing results, the ongoing treatment information, and the like.

Although the disclosure of network 1200 is made using a COVID-19 follow-up condition as an example, the disclosed embodiments may be adapted and implemented to predict follow-up conditions for other diseases. For example, the embodiments may be readily adapted for predicting follow-up conditions of an ICH and generating predicted 3D bleeding area images for the follow-up time steps.

According to certain embodiments, a non-transitory computer-readable medium may have a computer program stored thereon. The computer program, when executed by at least one processor, may perform a method for biomedical image analysis. For example, any of the above-described methods may be performed in this way.

In some embodiments, the computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

It will be apparent to those skilled in the art that various modifications and variations can be made to the disclosed system and related methods. Other embodiments will be apparent to those skilled in the art from consideration of the specification and practice of the disclosed system and related methods.

It is intended that the specification and examples be considered as exemplary only, with a true scope being indicated by the following claims and their equivalents.

What is claimed is:

1. A system for predicting a disease condition prediction from images of a patient, comprising:
   a communication interface configured to receive a sequence of images acquired of the patient by an image acquisition device, wherein the sequence of images are acquired at a sequence of prior time points during progression of a disease; and
   at least one processor, configured to:
      determine regions of interest based on the sequence of images acquired at the sequence of prior time points;
      apply a progressive condition prediction network to the regions of interest to predict a level of disease progression at a future time point during the progression of the disease, wherein to apply the progressive condition network to the regions of interest, the at least one processor is configured to:
         predict the level of disease progression at the future time point based on disease conditions at the sequence of prior time points and the regions of interest by applying the progressive condition prediction network comprising a convolutional recurrent neural network (ConvRNN) layer, a recurrent neural network (RNN) layer separate from the ConvRNN layer, and a plurality of fully connected layers receiving inputs from both the ConvRNN layer and the RNN layer; and
      provide a diagnostic output based on the predicted level of disease progression at the future time point.

2. The system of claim 1, wherein the sequence of images are 3D lung images acquired of a lung of the patient during progression of a lung disease, wherein the regions of interest are 3D lesion regions of interest determined from the 3D lung images.

3. The system of claim 2, wherein the lung disease is a COVID-19 disease, wherein the predicted level of disease progression is a progression level of the COVID-19 disease at the future time point.

4. The system of claim 1, wherein the at least one processor is further configured to apply the progressive condition prediction network to the regions of interest to sequentially predict levels of disease progression at a sequence of future time points during the progression of the disease.

5. The system of claim 1, wherein the ConvRNN layer comprises a plurality of ConvRNN units each corresponding to a time point, wherein the time point is one of the prior time points or the future time point,
   wherein the at least one processor is further configured to apply each ConvRNN unit to the region of interest for the corresponding time point and an output provided by another ConvRNN unit corresponding to an antecedent time point, to predict the region of interest for a subsequent time point.

6. The system of claim 5, wherein the RNN layer comprises a plurality of RNN units each corresponding to a time point, wherein the time point is one of the prior time points or the future time point, wherein the at least one processor is further configured to apply each RNN unit to the disease condition at the corresponding time point and an output provided by another RNN unit corresponding to an antecedent time point, to generate a feature map.

7. The system of claim 6, wherein plurality of fully connected layers comprise a first fully connected layer, a second fully connected layer, and a third fully connected layer, wherein the at least one processor is further configured to:
  apply the first fully connected layer to the feature map generated by the RNN unit, to generate a first vector;
  apply the second fully connected layer to the region of interest for the subsequent time point predicted by the ConvRNN unit, to generate a second vector; and
  apply the third fully connected layer to the first vector and the second vector determine the disease condition at the subsequent time point.

8. The system of claim 6, wherein each RN N unit is a long short-term memory (LSTM) RNN, a gate recurrent unit (GRU), a convolutional GRU, or a convolutional LSTM RNN.

9. The system of claim 1, wherein the communication interface is further configured to receive patient data of the patient, wherein the patient data comprises information of an ongoing treatment for the disease,
  wherein the at least one processor is further configured to apply the progressive condition prediction network additionally to the patient data in order to predict the level of disease progression at the future time point.

10. The system of claim 9, wherein the patient data includes at least one of demographic information of the patient, a disease history of the patient, or laboratory testing results of the patient.

11. The system of claim 1, wherein to determine a region of interest based on a corresponding image acquired at a prior time point, the at least one processor is configured to apply a lesion detection network to the corresponding image acquired at the prior time point, wherein the lesion detection network includes at least one lesion mask generator and at least one discriminator.

12. A method for disease condition prediction from images of a patient, comprising:
  receiving, by a communication interface, a sequence of images acquired of the patient by an image acquisition device, wherein the sequence of images are acquired at a sequence of prior time points during progression of a disease;
  determining, by at least one processor, regions of interest based on the sequence of images acquired at the sequence of prior time points;
  applying, by the at least one processor, a progressive condition prediction network to the regions of interest to predict a level of disease progression at a future time point during the progression of the disease, comprising:
    predicting the level of disease progression at the future time point based on disease conditions at the sequence of prior time points and the regions of interest by applying the progressive condition prediction network comprising a convolutional recurrent neural network (ConvRNN) layer, a recurrent neural network (RNN) la Ter separate from the ConvRNN layer, and a plurality of fully connected layers receivin inputs from both the ConvRNN layer and the RNN layer; and
  providing a diagnostic output based on the predicted level of disease progression at the future time point.

13. The method of claim 12, wherein the sequence of images are 3D lung images acquired of a lung of the patient during progression of a lung disease, wherein the regions of interest are 3D lesion regions of interest determined from the 3D lung images,
  wherein the lung disease is a COVID-19 disease, wherein the predicted level of disease progression is a progression level of the COVID-19 disease at the future time point.

14. The method of claim 12, further comprising applying the progressive condition prediction network to the regions of interest to sequentially predict levels of disease progression at a sequence of future time points during the progression of the disease.

15. The method of claim 12, wherein the ConvRNN layer comprises a plurality of ConvRNN units each corresponding to a time point, wherein the time point is one of the prior time points or the future time point,
  wherein applying the progressive condition prediction network to the regions of interest further comprises applying each ConvRNN unit to the region of interest for the corresponding time point and an output provided by another ConvRNN unit corresponding to an antecedent time point, to predict the region of interest for a subsequent time point.

16. The method of claim 15, wherein the RNN layer comprises a plurality of RNN units each corresponding to a time point, wherein the time point is one of the prior time points or the future time point,
  wherein applying the progressive condition prediction network to the regions of interest further comprises applying each RNN unit to the disease condition at the corresponding time point and an output provided by another RNN unit corresponding to an antecedent time point, to generate a feature map.

17. The method of claim 16, wherein the plurality of fully connected layers comprise a first fully connected layer, a second fully connected layer, and a third fully connected layer, wherein applying the progressive condition prediction network to the regions of interest further comprises:
  applying the first fully connected layer to the feature map generated by the RNN unit, to generate a first vector;
  applying the second fully connected layer to the region of interest for the subsequent time point predicted by the ConvRNN unit, to generate a second vector; and
  applying the third fully connected layer to the first vector and the second vector to determine the disease condition at the subsequent time point.

18. The method of claim 12, further comprising receiving patient data of the patient, wherein the patient data comprises information of an ongoing treatment for the disease,
  wherein the progressive condition prediction network is additionally applied to the patient data in order to predict the level of disease progression at the future time point.

19. A method for a COVID-19 condition prediction from lung images of a patient, comprising:
  receiving, by a communication interface, a sequence of lung images acquired of a lung of the patient by an image acquisition device, wherein the sequence of images are acquired at a sequence of prior time points during progression of a COVID-19 disease;
  determining, by at least one processor, regions of interest based on the sequence of lung images acquired at the sequence of prior time points, wherein each region of interest comprise the lung;

applying, by the at least one processor, a progressive condition prediction network to the regions of interest to predict a progression level of the COVID-19 disease at a future time point during the progression of the COVID-19 disease, comprising:
  predicting the progression level of the COVID-19 disease at the future time point based on disease conditions at the sequence of prior time points and the regions of interest by applying the progressive condition prediction network comprising a convolutional recurrent neural network (ConvRNN) layer a recurrent neural network (RNN) layer separate from the ConvRNN layer, and a plurality of fully connected layers receiving inputs from both the ConvRNN layer and the RNN layer; and
providing a diagnostic output based on the predicted progression level of the COVID-19 disease at the future time point.

20. The method of claim 19, wherein the RNN layer comprises a plurality of RNN units each corresponding to a time point, wherein the time point is one of the prior time points or the future time point,
  wherein applying the progressive condition prediction network to the regions of interest further comprises applying each RNN unit to a COVID-19 condition at the corresponding time point and an output provided by another RNN unit corresponding to an antecedent time point; to determine a COVID-19 condition at a subsequent time point.

* * * * *